United States Patent
Chen et al.

(10) Patent No.: US 12,295,985 B2
(45) Date of Patent: *May 13, 2025

(54) METHODS OF REDUCING SEVERITY OF GLAUCOMA BY INTRAVITREAL ADMINISTRATION OF INSULIN-LIKE GROWTH FACTOR BINDING PROTEIN-LIKE 1 (IGFBPL1)

(71) Applicant: The Schepens Eye Research Institute, Inc., Boston, MA (US)

(72) Inventors: Dong Feng Chen, Newtonville, MA (US); Chenying Guo, Malden, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 167 days.

This patent is subject to a terminal disclaimer.

(21) Appl. No.: 18/073,951

(22) Filed: Dec. 2, 2022

(65) Prior Publication Data
US 2023/0277623 A1 Sep. 7, 2023

Related U.S. Application Data

(63) Continuation of application No. 17/070,596, filed on Oct. 14, 2020, now abandoned, which is a
(Continued)

(51) Int. Cl.
| | |
|---|---|
| A61K 38/18 | (2006.01) |
| A61K 31/00 | (2006.01) |
| A61K 31/352 | (2006.01) |
| A61K 31/7004 | (2006.01) |
| A61K 31/708 | (2006.01) |
| A61K 31/7088 | (2006.01) |
| A61K 31/7105 | (2006.01) |
| A61K 31/711 | (2006.01) |
| A61K 31/713 | (2006.01) |
| A61K 38/00 | (2006.01) |
| A61K 38/17 | (2006.01) |
| A61K 38/19 | (2006.01) |
| A61K 38/20 | (2006.01) |
| A61K 38/21 | (2006.01) |
| A61K 38/22 | (2006.01) |
| A61K 38/30 | (2006.01) |
| A61K 45/06 | (2006.01) |
| C07K 14/00 | (2006.01) |
| C07K 14/47 | (2006.01) |
| C07K 14/48 | (2006.01) |
| A61K 9/00 | (2006.01) |
| A61K 9/51 | (2006.01) |
| A61K 35/30 | (2015.01) |
| A61K 48/00 | (2006.01) |
| A61K 49/00 | (2006.01) |

(Continued)

(52) U.S. Cl.
CPC .............. *A61K 38/18* (2013.01); *A61K 31/00* (2013.01); *A61K 31/352* (2013.01); *A61K 31/7004* (2013.01); *A61K 31/708* (2013.01); *A61K 31/7088* (2013.01); *A61K 31/7105* (2013.01); *A61K 31/711* (2013.01); *A61K 31/713* (2013.01); *A61K 38/1738* (2013.01); *A61K 38/1841* (2013.01); *A61K 38/2278* (2013.01); *A61K 38/30* (2013.01); *A61K 45/06* (2013.01); *A61K 9/0019* (2013.01); *A61K 9/0048* (2013.01); *A61K 9/0085* (2013.01); *A61K 9/5169* (2013.01); *A61K 35/30* (2013.01); *A61K 38/1703* (2013.01); *A61K 38/1709* (2013.01); *A61K 38/22* (2013.01); *A61K 48/00* (2013.01); *A61K 49/0056* (2013.01); *A61K 2300/00* (2013.01); *C12N 5/0621* (2013.01); *C12N 5/0623* (2013.01); *C12N 2501/105* (2013.01); *C12N 2502/08* (2013.01); *C12N 2502/081* (2013.01); *C12N 2533/50* (2013.01); *G01N 33/5058* (2013.01); *G01N 33/5073* (2013.01); *Y02A 50/30* (2018.01)

(58) Field of Classification Search
CPC .... A61K 38/00; A61K 38/18; A61K 38/1709; A61K 48/00; A61K 2300/00; A61K 35/30; A61K 9/0085; A61P 25/00; A61P 27/00; C12N 5/063; C12N 2502/08; C12N 5/0621; C12N 2533/50; G01N 33/5058; G01N 33/5073
See application file for complete search history.

(56) References Cited

U.S. PATENT DOCUMENTS

| | | |
|---|---|---|
| 4,522,811 A | 6/1985 | Eppstein et al. |
| 4,816,397 A | 3/1989 | Boss et al. |

(Continued)

FOREIGN PATENT DOCUMENTS

| | | |
|---|---|---|
| JP | 2013-529292 | 7/2013 |
| WO | WO 1994/023697 | 10/1994 |

(Continued)

OTHER PUBLICATIONS

Burgess et al. J of Cell Bio. 1990, 111:2129-2138.*
(Continued)

*Primary Examiner* — Chang-Yu Wang
(74) *Attorney, Agent, or Firm* — Fish & Richardson P.C.

(57) ABSTRACT

Disclosed is a method of promoting neuronal growth by administering IGFBPL-1, or an agent that increases or stabilizes IGFBPL-1 activity to a subject in need thereof, e.g., a subject in need of treating optic nerve degeneration.

12 Claims, 18 Drawing Sheets
Specification includes a Sequence Listing.

Related U.S. Application Data continuation of application No. 14/002,033, filed as application No. PCT/US2012/026931 on Feb. 28, 2012, now Pat. No. 10,842,849.

(60) Provisional application No. 61/447,314, filed on Feb. 28, 2011.

(51) Int. Cl.
| | |
|---|---|
| C12N 5/079 | (2010.01) |
| C12N 5/0797 | (2010.01) |
| G01N 33/50 | (2006.01) |

(56) References Cited

U.S. PATENT DOCUMENTS

| | | | |
|---|---|---|---|
| 4,816,567 | A | 3/1989 | Cabilly et al. |
| 4,883,666 | A | 11/1989 | Sabel et al. |
| 4,975,369 | A | 12/1990 | Beavers et al. |
| 4,978,745 | A | 12/1990 | Schoemaker et al. |
| 5,443,505 | A | 8/1995 | Wong et al. |
| 5,455,044 | A | 10/1995 | Kim et al. |
| 5,576,018 | A | 11/1996 | Kim et al. |
| 5,766,242 | A | 6/1998 | Wong et al. |
| 6,071,889 | A | 6/2000 | Weiss et al. |
| 6,251,090 | B1 | 6/2001 | Avery et al. |
| 6,299,895 | B1 | 10/2001 | Hammang et al. |
| 6,375,972 | B1 | 4/2002 | Guo et al. |
| 6,413,540 | B1 | 7/2002 | Yaacobi |
| 6,416,777 | B1 | 7/2002 | Yaacobi |
| 6,468,798 | B1 | 10/2002 | Debs et al. |
| 6,596,296 | B1 | 7/2003 | Nelson et al. |
| 7,109,030 | B2 | 9/2006 | Dedera et al. |
| 7,232,880 | B2 | 6/2007 | Oh et al. |
| 7,238,529 | B2 | 7/2007 | Benowitz et al. |
| 7,514,532 | B2 | 4/2009 | Oh et al. |
| 7,585,497 | B2 | 9/2009 | Oh et al. |
| 7,714,102 | B2 | 5/2010 | Oh et al. |
| 7,780,949 | B2 | 8/2010 | Riser |
| 8,198,284 | B2 | 6/2012 | Shie et al. |
| 8,470,295 | B2 | 6/2013 | Warren et al. |
| 10,842,849 | B2 | 11/2020 | Chen et al. |
| 2003/0017513 | A1 | 1/2003 | Khosravi et al. |
| 2004/0067882 | A1 | 4/2004 | Alsobrook et al. |
| 2005/0256059 | A1 | 11/2005 | Benowitz |
| 2006/0073514 | A1 | 4/2006 | Dedera et al. |
| 2006/0276394 | A1 | 12/2006 | Aston et al. |
| 2008/0193446 | A1 | 8/2008 | Phillips |
| 2008/0253989 | A1 | 10/2008 | Ahmed et al. |
| 2009/0156496 | A1 | 6/2009 | Benowitz et al. |
| 2010/0120143 | A1 | 5/2010 | Oh et al. |
| 2010/0166713 | A1 | 7/2010 | Dalton et al. |
| 2012/0156216 | A1 | 6/2012 | Oh |
| 2013/0216504 | A1 | 8/2013 | Riser |
| 2014/0005098 | A1 | 1/2014 | Godeau et al. |
| 2014/0128322 | A1 | 5/2014 | Chen et al. |
| 2014/0286906 | A1 | 9/2014 | Bilbao Cortes et al. |
| 2022/0143139 | A1 | 5/2022 | Chen et al. |

FOREIGN PATENT DOCUMENTS

| | | |
|---|---|---|
| WO | WO 1995/013796 | 5/1995 |
| WO | WO 1997/003652 | 2/1997 |
| WO | WO 2000/040089 | 7/2000 |
| WO | WO 2001/002847 | 1/2001 |
| WO | WO 2002/089767 | 11/2002 |
| WO | WO 2003/040330 | 5/2003 |
| WO | WO 2003/041655 | 5/2003 |
| WO | WO 2004/073551 | 9/2004 |
| WO | WO 2005/005635 | 1/2005 |
| WO | WO 2005/048914 | 6/2005 |
| WO | WO 2007/014323 | 2/2007 |
| WO | WO 2012/118796 | 9/2012 |
| WO | WO 2012/118863 | 9/2012 |
| WO | WO 2017/213504 | 12/2017 |
| WO | WO 2022/256331 | 12/2022 |

OTHER PUBLICATIONS

Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Abbs et al., "Sparing of first dose effect of monovalent anti-CD3 antibody used in allograft rejection is associated with diminished release of pro-inflammatory cytokines," Ther. Immunol., Dec. 1994, 1(6):325-31.
Adeluyi et al., "Microglia morphology and proinflammatory signaling in the nucleus accumbens during nicotine withdrawal," Science Advances, Oct. 2019, 5(10):eaax7031, 11 pages.
Benjamini and Hochberg, "Controlling the false discovery rate: a practical and powerful approach to multiple testing," Journal of the Royal statistical society: series B (Methodological), 1995, 57(1):289-300.
Bolstad et al., "A comparison of normalization methods for high density oligonucleotide array data based on variance and bias," Bioinformatics, Jan. 2003, 19(2):185-93.
Bourges et al., "Ocular drug delivery targeting the retina and retinal pigment epithelium using polylactide nanoparticles," Invest Opth Vis Sci., Aug. 2003, 44:3562-9.
Butovsky and Weiner, "Microglial signatures and their role in health and disease," HHS Public Access Author Manuscript, doi: 10.1038/s41583-018-0057-5, published online May 28, 2020, published in final edited form as: Nat Rev Neurosci, Oct. 2018, 19(10):622-635, 33 pages.
Chen et al., "Optic neuropathy due to microbead-induced elevated intraocular pressure in the mouse," Invest Ophthalmol Vis Sci., Jan. 2011, 52(1):36-44.
Chesler et al., "Complex trait analysis of gene expression uncovers polygenic and pleiotropic networks that modulate nervous system function," Nature Genetics, Feb. 2005, 37(3):233-242.
Cianciulli et al., "Microglia Mediated Neuroinflammation: Focus on PBK Modulation," Biomolecules, Jan. 2020, 10(1):137, 19 pages.
Colcher et al., "Single-Chain Antibodies in Pancreatic Cancer," Ann. N. Y. Acad. Sci., Jun. 1999, 880(1):263-80.
Colonna and Butovsky, "Microglia Function in the Central Nervous System During Health and Neurodegeneration," Annu Rev Immunol., Apr. 2017, 35:441-468.
Freeman et al., "Genetic networks in the mouse retina: growth associated protein 43 and phosphatase tensin homolog network," Mol Vis., May 2011, 17:1355-1372.
Geisert et al., "Gene expression in the mouse eye: an online resource for genetics using 103 strains of mice," Mol Vis., Aug. 2009, 15:1730-1763.
Hammond et al., "Immune Signaling in Neurodegeneration," Immunity, Apr. 2019, 50(4):955-974.
Homayouni et al., "Gene clustering by latent semantic indexing of MEDLINE abstracts," Bioinformatics, Jan. 2005, 21(1):104-15.
Huang et al., "Placental growth factor negatively regulates retinal endothelial cell barrier function through suppression of glucose-6-phosphate dehydrogenase and antioxidant defense systems," FASEB Journal, Dec. 2019, 33(12):13695-13709, 29 pages.
Huang et al., "The DAVID Gene Functional Classification Tool: a novel biological module-centric algorithm to functionally analyze large gene lists," Genome Biology, Sep. 2007, 8:R183, 16 pages.
International Preliminary Report on Patentability in International Appln. No. PCT/US2022/031615, mailed Dec. 14, 2023, 7 pages.
Jones et al., "Replacing the complementarity-determining regions in a human antibody with those from a mouse," Nature, 1986, 321(6069):522-5.
Jung et al., "Analysis of fractalkine receptor $CX_3CR1$ function by targeted deletion and green fluorescent protein reporter gene insertion," Mol Cell Biol, Jun. 2000, 20(11):4106-4114.
Kim and Kim, "Anti-breast cancer activity of Fine Black ginseng (Panax ginseng Meyer) and ginsenoside Rg5," J Ginseng Res., Apr. 2015, 39(2):125-34.
Li and Barres, "Microglia and macrophages in brain homeostasis and disease," Nat Rev Immunol., Apr. 2018, 18(4):225-242.

(56) References Cited

OTHER PUBLICATIONS

Lian et al., "Protocol for Primary Microglial Culture Preparation," Bio Protoc., Nov. 2016, 6(21):e1989, 8 pages.
Liao et al., "featureCounts: an efficient general purpose program for assigning sequence reads to genomic features," Bioinformatics, Apr. 2014, 30(7):923-30.
Liddelow et al., "Neurotoxic Reactive Astrocytes are Induced by Activated Microglia," Nature, 2017, 541(7638):481-487, 25 pages.
Love et al., "Moderated estimation of fold change and dispersion for RNA-seq data with DESeq2," Genome Biol., 2014, 15(12):550, 21 pages.
Magni et al., "Parthenolide inhibits the LPS-induced secretion of IL-6 and TNF-α and NF-κB nuclear translocation in BV-2 microglia," Phytotherapy Research., Sep. 2012, 26(9):1405-1409, 5 pages.
Morrison and Oi, "Genetically Engineered Antibody Molecules," Adv. Immunol., 1989, 44:65-92.
Morrison et al., "Chimeric human antibody molecules: mouse antigen-binding domains with human constant region domains," Proc. Natl. Acad. Sci., USA, Nov. 1984, 81(21):6801-5.
Ngolab et al., "Reflections on the Utility of 30 the Retina as a Biomarker for Alzheimer's Disease: A Literature Review," Neurology and Therapy, Dec. 2019, 8(Suppl 2):57-72.
Nishimura et al., "Recombinant human-mouse chimeric monoclonal antibody specific for common acute lymphocytic leukemia antigen," Cancer Research, Feb. 1987, 47(4):999-1005.
Normando et al., "The retina as an early biomarker of neurodegeneration in a rotenone-induced model of Parkinson's disease: evidence for a neuroprotective effect of rosiglitazone in the eye and brain," Acta Neuropathologica Communications, Aug. 2016, 4(1):86, 15 pages.
Padlan, "Anatomy of the antibody molecule," Molec. Immun., Feb. 1994, 31(3):169-217.
Pan et al., "IGFBPL 1 is a master driver of microglia homeostasis and resolution of neuroinflammation in glaucoma and brain tauopathy," Cell Rep., Aug. 2023, 42(8):112889, 29 pages.
Pickett et al., "Amyloid beta and tau cooperate to cause reversible behavioral and transcriptional deficits in a model of Alzheimer's disease," Cell Rep., Dec. 2019, 29(11):3592-3604.e5.
Płóciennik et al., "Activated caspase-3 and neurodegeneration and synaptic plasticity in Alzheimer's disease," Advances in Alzheimer's Disease, Jan. 2015, 4(3):63-77.
Queen et al., "A humanized antibody that binds to the interleukin 2 receptor," Proc. Natl. Acad. Sci. USA, Dec. 1989, 86(24):10029-33.
Reiter and Pastan, "Antibody engineering of recombinant Fv immunotoxins for improved targeting of cancer: disulfide-stabilized Fv immunotoxins," Clin. Cancer Res., Feb. 1996, 2(2):245-52.
Riechmann et al., "Reshaping human antibodies for therapy," Nature, Mar. 1988, 332(6162):323-7.
Ronning et al., "Molecular profiling of resident and infiltrating mononuclear phagocytes during rapid adult retinal degeneration using single-cell RNA sequencing," Scientific Reports, Mar. 2019, 9(1):4858, 12 pages.
Shi et al., "Optimization of Optomotor Response-based Visual Function Assessment in Mice," Sci Rep., 2018, 8:9708, 10 pages.
Short, "Safety Evaluation of Ocular Drug Delivery Formulations: Techniques and Practical Considerations," Toxicol Pathol., Jan. 2008, 36(1):49-6.
Stuart et al., "Comprehensive Integration of Single-Cell Data," Cell, Jun. 2019, 177(7):1888-1902.e21, 37 pages.
Tang et al., "Therapeutic Targeting of Retinal Immune Microenvironment With CSF-1 Receptor Antibody Promotes Visual Function Recovery After Ischemic Optic Neuropathy," Front Immunol., Nov. 2020, 11:585918, 15 pages.
Tian et al., "Current perspective of neuroprotection and glaucoma," Clin Ophthalmol., Nov. 2015, 9:2109-18.
Ugradar et al., "Teprotumumab for non-inflammatory thyroid eye disease (TED): evidence for increased IGF-IR expression," Eye (Lond)., Sep. 2021, 35(9):2607-2612.
Verhoeyen et al., "Reshaping human antibodies: grafting an antilysozyme activity," Science, Mar. 1988, 239(4847):1534-6.
Vijaya et al., "Prevalence and causes of low vision and blindness in an urban population: The Chennai Glaucoma Study," Indian J Ophthalmol., Apr. 2014, 62(4):477-481.
Wei et al., "Neuroglobin is an endogenous neuroprotectant for retinal ganglion cells against glaucomatous damage," Am J Pathol., Dec. 2011, 179(6):2788-2797.
Ambati et al., "Diffusion of high molecular weight compounds through sclera," Invest. Ophthalmol. Vis. Sci., Apr. 2000, 41(5):1181-1185.
Ambati et al., "Transscleral delivery of bioactive protein to the choroid and retina," Invest. Ophthalmol. Vis. Sci., Apr. 2000, 41(5):1186-1191.
Bell et al., "Does autoimmunity play a part in the pathogenesis of glaucoma?," Prog. Retin. Eye Res., Sep. 2013, 36:199-216.
Benny et al., "Continuous Delivery of Endogenous Inhibitors from Poly (Lactic-Co-Glycolic Acid) Polymeric Microspheres Inhibits Glioma Tumor Growth," Clinical Cancer Research, Jan. 2005, 11(2):768-776.
Bessero et al., "Neuroprotection for optic nerve disorders," Curr. Opin. Neurol., 2010, 23(1):10-15.
Blight, "Miracles and molecules—progress in spinal cord repair," Nat. Neurosci., 2002, 5:1051-1054.
Boughton, "Traumatic Optic Neuropathy: Previous Therapies Now Questioned or Shelved, " EyeNet Magazine, 2009, retrieved on Jan. 10, 2019, retrieved from URL <https://www.aao.org/eyenet/article/traumatic-optic-neuropathy-previous-therapies-now->, 9 pages.
Bowie et al., "Deciphering the Message in Protein Sequences: Tolerance to Amino Acid Substitutions," Science, 1990, 247:1306-1310.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Bio., 1990, 111:2129-2138.
Chen et al., "Commensal microflora-induced T cell responses mediate progressive neurodegeneration in glaucoma," Nat Commun., Aug. 2018, 9(1):3209, 13 pages.
Cho et al., "IGFBPL1 protects against the neuronal and vision loss in IGFBPL1-/- mice with ocular hypertension," Abstract, Presented at 2019 ARVO Annual Meeting, Vancouver, B.C., Apr. 28-May 2, 2019; Investigative Ophthalmology & Visual Science, Jul. 2019, 60(9):615, 2 pages.
Dahlmann-Noor et al., "Current approaches and future prospects for stem cell rescue and regeneration of the retina and optic nerve," Can J. Ophthalmol., 2010, 45:333-341.
Deumens et al., "Alignment of Glial Cells Stimulates Directional Neurite Growth of CNS Neurons In Vitro," Neuroscience, 2004, 125(3):591-604.
Dick et al., "Miniaturization in Glaucoma Monitoring and Treatment: A Review of New Technologies That Require a Minimal Surgical Approach," Ophthalmol. Ther., 2019, 8:19-30.
Doudet et al., "PET Imaging of Implanted Human Retinal Pigment Epithelial Cells in the MPTP-Induced Primate Model of Parkinson's Disease," Experimental Neurology, Oct. 2004, 189(2):361-368.
Dubois et al., "Research Criteria for the Diagnosis of Alzheimer's Disease: Revising the NINCDS-ADRDA Criteria," The Lancet Neurology, Aug. 2007, 6(8):734-746.
Fischer et al., "Drug Delivery to the Posterior Segment of the Eye, " Eur J Ophthalmol., 2011, 21(Suppl 6):S20-26.
Flammer et al., "What is the present pathogenetic concept of glaucomatous optic neuropathy?," Surv Ophthalmol., Nov. 2007, 52(Suppl 2):S162-73.
Gasco et al., "Microemulsions as topical delivery vehicles: Ocular administration of timolol," J. Pharma Biomed Anal., 1989, 7(4):433-439.
Gaudana et al., "Ocular Drug Delivery," AAPS J., Sep. 2010, 12(3):348-360.
GenBank Accession No. CAA24998.1, "Insulin-like Growth Factor 1A Precursor [*Homo Sapiens*]", dated Oct. 7, 2008, 2 pages.
GenBank Accession No. NM_001007563.2, "*Homo Sapiens* Insulin Like Growth Factor Binding Protein like 1 (IGFBPL 1), mRNA", dated Jun. 25, 2018, 3 pages.

(56) References Cited

OTHER PUBLICATIONS

GenBank Accession No. NP_001007564.1, "Insulin-Like Growth Factor-Binding Protein-Like 1 Precursor [*Homo Sapiens*]", Jun. 25, 2018, 2 pages.
GenBank Accession No. NP_002147.2, "chaperonin [*Homo sapiens*]," dated Feb. 14, 2010, 3 pages.
GenBank Accession No. WP_000729117.1, "MultiSpecies: chaperonin GroEL [Enterobacteriaceae]," dated Oct. 27, 2015, 1 page.
GenBank Accession No. X00173.1, "*Homo Sapiens* mRNA for Insulin-Like Growth Factor 1A Precursor, Complete CDS", Oct. 7, 2008, 2 pages.
Gonda et al., "Expression Profiles of Insulin-Like Growth Factor Binding Protein-Like 1 in the Developing Mouse Forebrain," Gene Expr. Patterns, Feb. 2007, 7(4):431-440.
Gramlich et al., "Enhanced Insight into the Autoimmune Component of Glaucoma: IgG Autoantibody Accumulation and Pro-Inflammatory Conditions in Human Glaucomatous Retina," PLoS One, 2013, 8(2):e57557, 11 pages.
Grotegut et al., "Abstract: Intravitreal HSP27 injection leads to retinal degeneration in rats," Abstract, Presented at Proceedings of the ARVO Annual Meeting, Vancouver, CA, Apr. 28-May 2, 2019; Investigative Ophthalmology and Visual Science, Jul. 2019, 60:4929, 2 pages.
Grus et al., "Autoimmunity and glaucoma," J Glaucoma, Jan. 2008, 17(1):79-84.
Guo et al., "A novel IGFBP like protein (IGFBPL-1) promotes axon outgrowth in retinal ganglion cells through the regulation of IGF-I signaling pathway," Abstract, Presented at Association for Research in Vision and Ophthalmology (ARVO) 2011 Annual Meeting, Fort Lauderdale, FL, May 1-2, 2011; Investigative Ophthalmology & Visual Science, Apr. 2011, 52:4675, 2 pages.
Guo et al., "Alzheimer's Disease and Retinal Neurodegeneration," Curr. Alzheimer's Research, 2010, 7:3-14.
Guo et al., "IGFBPL1 Regulates Axon Growth through IGF-1-mediated Signaling Cascades," Sci Rep., Feb. 2018, 8(1):2054, 13 pages.
Höke, "Mechanisms of Disease: what factors limit the success of peripheral nerve regeneration in humans?" Nat. Clin. Pract. Neurol., 2006, 2:448-454.
Hope et al., "Generation of Multilamellar and Unilamellar Phospholipid Vesicles", Chemistry and Physics of Lipids, Jun.-Jul. 1986, 40(2-4):89-107.
International Preliminary Report on Patentability in International Appln. No. PCT/US2012/026931, dated Sep. 12, 2013, 6 pages.
International Preliminary Report on Patentability in International Appln. No. PCT/US2020/020794, dated Sep. 16, 2021, 9 pages.
International Search Report and Written Opinion in International Appln. No. PCT/US2012/026931, dated May 31, 2012, 6 pages.
International Search Report and Written Opinion in International Appln. No. PCT/US2020/020794, dated Jun. 11, 2020, 11 pages.
International Search Report and Written Opinion in International Appln. No. PCT/US2022/031615, mailed on Oct. 18, 2022, 11 pages.
IrisVision.com [online], "Can Optic Nerve Damage be Treated?," Aug. 6, 2020, retrieved on Aug. 27, 2022, retrieved from URL<irisvision.com/can-optic-nerve-damage-be-treated/>, 8 pages.
Kubal, "Updated Imaging of Traumatic Brain Injury," Radiologic Clinics of North America, 2012, 50(1):15-41.
Lazorthes et al., "Advances in Drug Delivery Systems and Applications in Neurosurgery," Advances and Technical Standards in Neurosurgery, 1991, 18:143-192.
Losa et al., "Design of new formulations for topical ocular administration: polymeric nanocapsules containing metipranolol," Pharmaceutical Research, Jan. 1993, 10(1):80-87.
Margalit et al., "Retinal and Optic Nerve Diseases, " Artificial Organs, 2003, 27:963-974.
My.ClevelandClinic.org [online], "Leber Hereditary Optic Neuropathy (Sudden Vision Loss)," Feb. 26, 2021, retrieved on Aug. 27, 2022, retrieved from URL<my.clevelandclinic.org/health/diseases/15620-leber-hereditary-optic-neuropathy-sudden-vision-loss>, 13 pages.
Nei.Nih.gov [online], "Glaucoma," Apr. 21, 2022, retrieved on Aug. 27, 2022, retrieved from URL<www.nei.nih.gov/learn-about-eye-health/eye-conditions-and-diseases/glaucoma>, 6 pages.
Novak et al., "Huntington's Disease: Clinical Presentation and Treatment," International Review of Neurobiology, 2011, 98:297-323.
Novikova et al., "Biopolymers and Biodegradable Smart Implants for Tissue Regeneration After Spinal Cord Injury," Current Opinion in Neurology, Dec. 2003, 6(6):711-715.
Ommaya, "Implantable Devices for Chronic Access and Drug Delivery to the Central Nervous System," Cancer Drug Delivery, 1984, 1(2):169-179.
Pan et al., "A role for Insulin-like growth factor binding protein-like protein 1 in Microglia," Abstract, Presented at 2019 ARVO Annual Meeting, Vancouver, B.C., Apr. 28-May 2, 2019; Investigative Ophthalmology & Visual Science, Jul. 2019, 60(9):4008, 2 pages.
Pawson et al., "Assembly of Cell Regulatory Systems Through Protein Interaction Domains," Science, 2003, 300:445-452.
Peragallo et al., "Is there treatment for Leber Hereditary Optic Neuropathy?," Curr. Opin. Ophthalmol., 2015, 26:450-457.
Quigley et al., "The number of people with glaucoma worldwide in 2010 and 2020," Br J Ophthalmol., Mar. 2006, 90(3):262-7.
Schmidt et al., "Neural Tissue Engineering: Strategies for Repair and Regeneration," Annu. Rev. Biomed. Eng., 2003, 5:293-347.
Sherman et al., "Management of Traumatic Optic Neuropathy With Coexistent Spinal Cord Injury: A Case Report," Arch Phys Med Rehabil., 1997, 78(9):1012-1014.
Szoka et al., "Comparative Properties and Methods of Preparation of Lipid Vesicles (Liposomes)," Annual Review of Biophysics and Bioengineering, 1980, 9:467-508.
Tan et al., "Simulation of Intratumoral Release of Etanidazole: Effects of the Size of Surgical Opening," Journal of Pharmaceutical Sciences, Apr. 2003, 92(4):773-789.
Tangri and Khurana, "Basics of ocular drug delivery systems," Intl J Res Pharma Biomed Sci., Jan. 2011, 2(4): 1541-1552.
Tarride et al., "New Glaucoma Diagnostic Technologies: A Systematic Review of Economic Studies," Canadian Journal of Ophthalmology, Feb. 2011, 46(1):89-91.
Tezel et al., "The Immune System and Glaucoma," Current Opinion in Ophthalmology, Apr. 2004, 15(2):80-84.
't Hart et al., "The use of animal models to investigate the pathogenesis of neuroinflammatory disorders of the central nervous system," Curr. Opin. Neurol., 2003, 16:375-383.
Thee et al., "Immune tolerance to HSP60 attenuates neurodegeneration in a mouse model of glaucoma," Abstract, Presented at 2018 ARVO Annual Meeting, Honolulu, HI, Apr. 29-May 3, 2018; Investigative Ophthalmology & Visual Science, Jul. 2018, 59(9):6142, 2 pages.
Tóth et al., "Overexpression of Hsp27 ameliorates symptoms of Alzheimer's disease in APP/PS1 mice," Cell Stress Chaperones, Nov. 2013, 18(6):759-71.
Vu et al., "The Immunology of Glaucoma," Asia Pacific J. Ophthalmol., 2012, 1(5):303-311.
Walland et al., "Failure of medical therapy despite normal intraocular pressure," Clin Exp Ophthalmol., Dec. 2006, 34(9):827-36.
Wax, "The case for autoimmunity in glaucoma," Exp. Eye Res., Aug. 2011, 93(2):187-190.
Wei et al., "Abstract: A neuroprotective role of IGFBPL1 in glaucoma," Abstract, Presented at Proceedings of the ARVO Annual Meeting, Honolulu, HI, Apr. 29-May 3, 2018; Investigative Ophthalmology and Visual Science, Jul. 2018, 59:6128, 2 pages.
O'Reilly et al., "HspB1 (Hsp27) Expression and Neuroprotection in the Retina," Mol. Neurobiol., 2010, 42:124-132.
Johnson et al., "Rodent models of glaucoma," HHS Public Access Author Manuscript, doi: 10.1016/j.brainresbull.2009.04.004, published online Feb. 15, 2011; published in final edited form as: Brain Res Bull., Feb. 2010, 81(2-3):349-358, 20 pages.

* cited by examiner

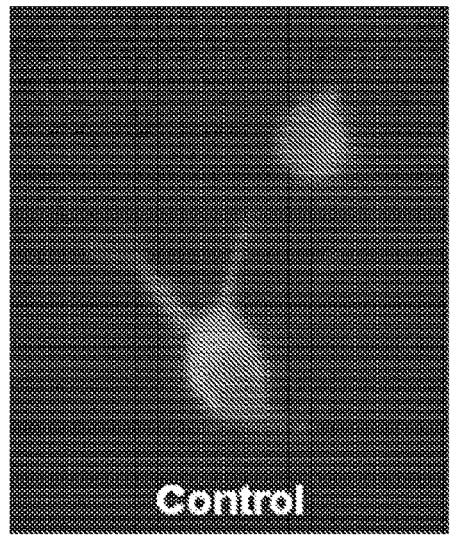 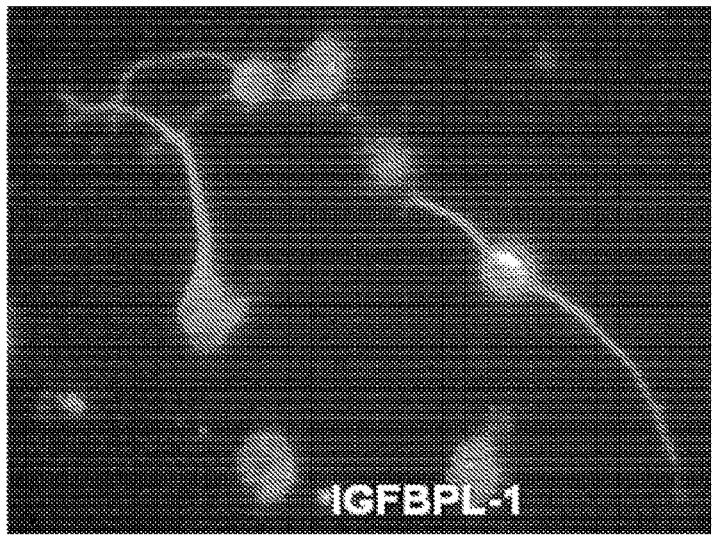
FIG. 3A  FIG. 3B
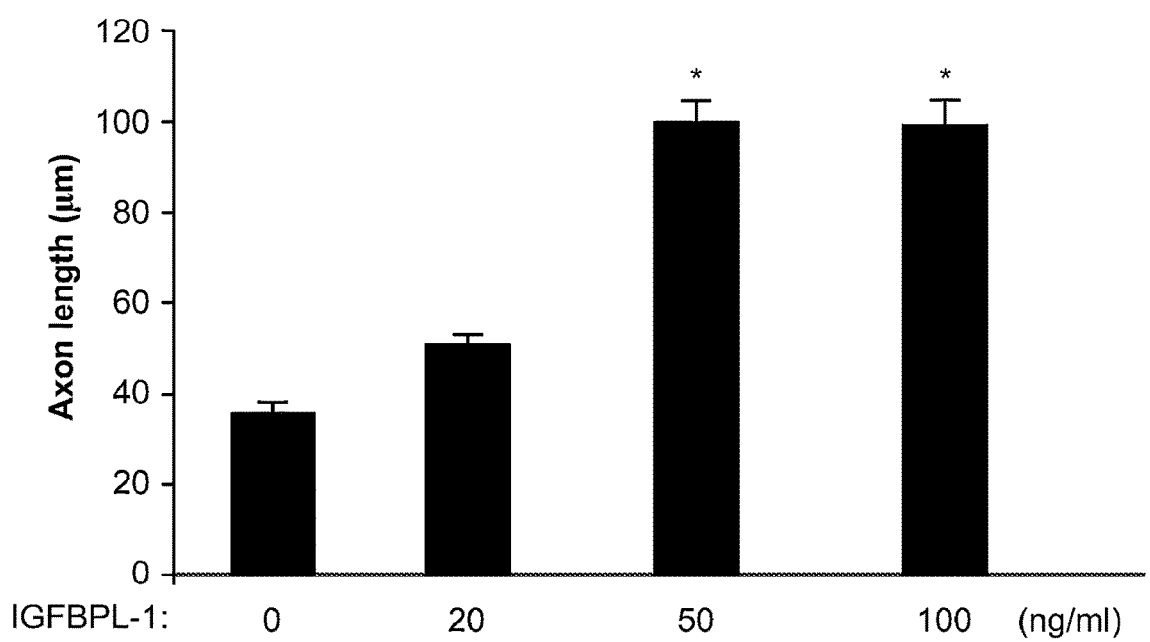
FIG. 4

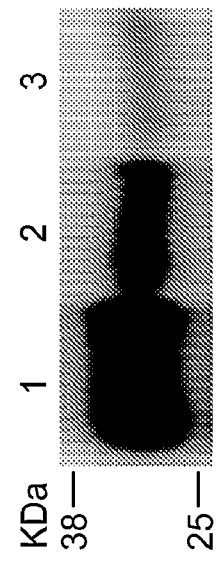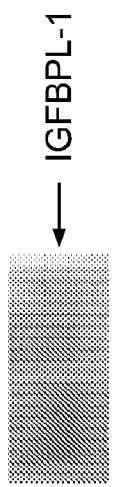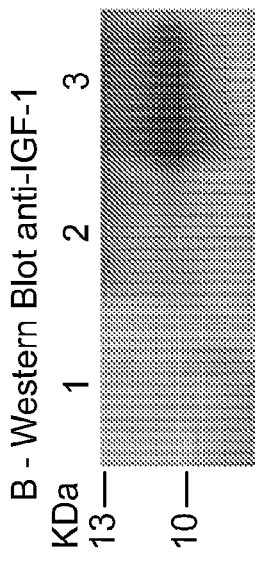
E18 retina lysates
A - Western Blot anti-IGFBPL-1
← IGFBPL-1
1  2
B - Western Blot anti-IGF-1
← IGF-1
1  2
1: IP anti - IGFBP-1
2: IP anti - IGF-1
FIG. 5 (II)
mouse recombinant IGFBPL-1 & IGF-I
A - Western Blot anti-IGFBPL-1
KDa
38 —
25 —
1  2  3
B - Western Blot anti-IGF-1
KDa
13 —
10 —
1  2  3
1 - Mouse IGFBPL-1 (Control no IP)
2 - IP anti-IGFBPL-1
3 - IP anti-IGF-1
FIG. 5 (I)

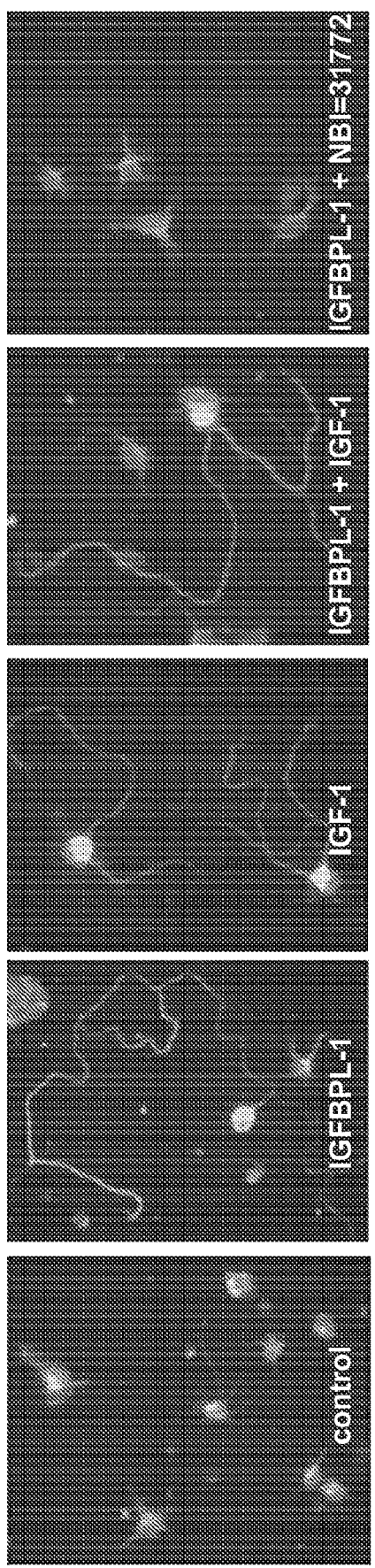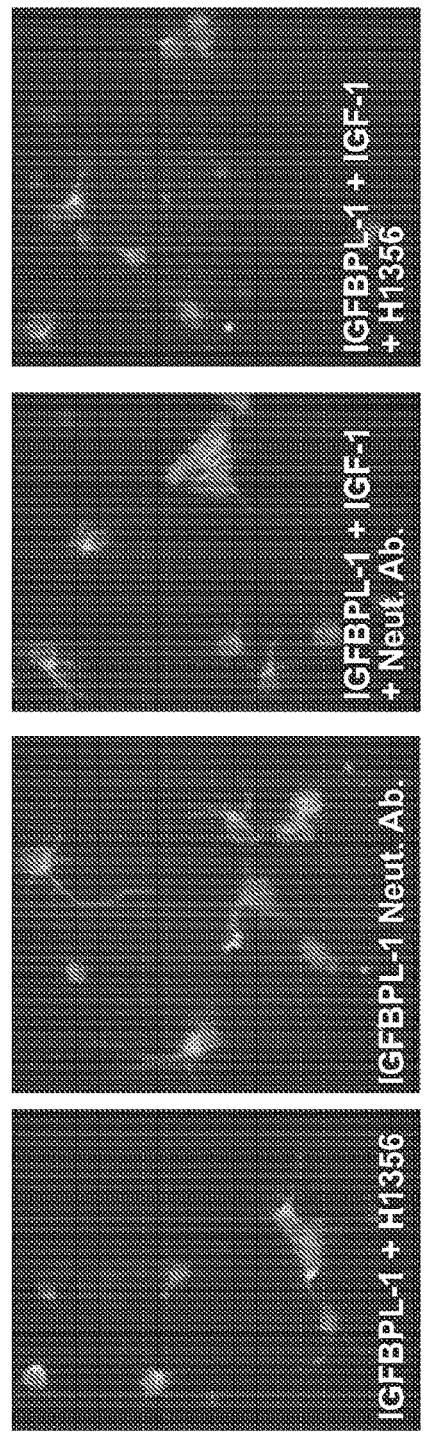

METHODS OF REDUCING SEVERITY OF GLAUCOMA BY INTRAVITREAL ADMINISTRATION OF INSULIN-LIKE GROWTH FACTOR BINDING PROTEIN-LIKE 1 (IGFBPL1)

RELATED APPLICATIONS

This application is a continuation application of U.S. patent application Ser. No. 17/070,596, filed Oct. 14, 2020, now abandoned, which is a continuation of U.S. patent application Ser. No. 14/002,033, filed Dec. 26, 2013, U.S. Pat. No. 10,842,849, which is a National Stage Application, filed under 35 U.S.C. § 371, of International Application No. PCT/US2012/026931, filed Feb. 28, 2012, which claims the benefit of priority under 35 U.S.C. § 119 (e) to U.S. Provisional Application No. 61/447,314, filed Feb. 28, 2011, which are incorporated herein by reference in their entireties.

STATEMENT AS TO FEDERALLY SPONSORED RESEARCH

This invention was made with government support under Grant numbers EY017641 and DA024803 awarded by the National Institutes of Health, Grant number W81XWH-09-2-0091 awarded by the Department of Defense, and Grant number 1I01RX000110 awarded by the Department of Veterans Affairs. The Government has certain rights in the invention.

INCORPORATION BY REFERENCE OF SEQUENCE LISTING

The contents of the text file named "00633-0298003_SL_ST26.xml", which was created on Dec. 2, 2022 and is 6,857 bytes in size, are hereby incorporated by reference in their entirety.

FIELD OF THE INVENTION

The invention relates to compositions for controlling neuronal outgrowth.

BACKGROUND OF THE INVENTION

Insulin Growth Factor 1 (IGF-1) is thought to play an important role in neuronal cell survival and nerve growth in development, and its effects are mainly mediated through its major receptor IGF-IR. However, the underlying mechanisms in which IGF-1 acts have not been fully understood, and tempts of applying IGF-1 to stimulate nerve regeneration and repair after injury have been unsuccessful. As such, there is a pressing need in the art to identify and characterize the role and mode of IGF-1 function in its regulation of neuronal cell survival and nerve regeneration in the postnatal stage and adult.

SUMMARY OF THE INVENTION

The present invention is based in part on the discovery that insulin-like growth factor binding protein-like 1 (IGFBPL1) is a key factor in promoting axon outgrowth in retinal ganglion cells (RGCs) through the regulation of IGF-1 signaling pathway. In the absence of IGFBPL1, administration of IGF-1 alone fails to stimulate RGC axon growth. Applying IGFBPL1, or an agent that increases or stabilizes IGFBPL1 activity or expression reverses the developmental loss of axon regenerative capacity. As described herein, these compounds decrease optic nerve degeneration, and increase optic nerve growth and regeneration through regulation of the IGF-1 signaling pathway. Specifically, the compounds described herein treat diseases or injuries that can cause optic nerve degeneration or axon degeneration in the peripheral and central nervous system (CNS), such as traumatic brain injury, spinal cord injury, multiple sclerosis, Alzheimer's disease, and Parkinson's disease.

The invention features a method of promoting nerve growth or regeneration, e.g., nerve fiber outgrowth of a neuron, neural progenitor cell or stem cell in a subject. The subject is preferably a mammal or bird in need of such treatment, e.g., a subject that has been diagnosed with optic nerve degeneration or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human. The method comprises contacting the neuron, neural progenitor cell or stem cell with an effective amount of an agent that increases IGFBPL1 levels or activity, thereby promoting nerve fiber outgrowth of the neuron or cell differentiation or trans-differentiation into a neuron that is capable of extending nerve fibers. The contacting occurs in vivo, in vitro, or ex vivo (e.g., using explanted patient tissue). For example, the agent is IGFBPL1 protein or a fragment there of or a nucleic acid that encodes IGFBPL1 or a fragment thereof. Alternatively, the agent is an IGFBPL1 agonist.

In some cases, the agent is contacted in the absence of xanthine oxidase and/or in the absence of exogenous nerve growth factor (NGF), and/or in the absence of exogenous D-mannose, and/or in the absence of exogenous oncomodulin, and/or in the absence of exogenous TGF-B, and/or in the absence of IGF-1.

An exemplary to be treated neuron is an optic nerve neuron, a retinal neuron, or a neuron of any type (which can include sensory and motor neurons, or neurons in the brain and spinal cord). In some cases, the neuron is an injured neuron or a diseased neuron. For example, the neuron is selected from the group consisting of central nervous system (CNS) neuron and peripheral nervous system (PNS) neuron. Other suitable neurons include an optic nerve neuron and a retinal neuron.

In some cases, the optic nerve neuron is an injured neuron, and injury to the optic nerve neuron is the result of branch and central vein/artery occlusion, blast injury, trauma, ischemia, edema, tumor, secondary glaucoma, congenital glaucoma, angle-closure glaucoma, open-angle glaucoma, optic neuritis, or Leber's hereditary optic neuropathy. Alternatively, the retinal neuron is injured as the result of macular degeneration, age related macular degeneration, retinitis pigmentosa, photoreceptor dystrophy, diabetic retinopathy, retinal edema, retinal detachments, damage associated with laser therapy, and surgical light-induced iatrogenic retinopathy.

In one aspect, the subject suffers from neurological injury that results from a disease or condition of the subject. The disease or condition can be any condition, e.g., stroke, trauma, blast injury, amyotrophic lateral sclerosis (ALS), multiple sclerosis, traumatic brain injury, tumor, ischemia, spinal cord injury, Huntington's disease, Parkinson's disease, Alzheimer's disease, multiple sclerosis, multiple system atrophy (MSA), spino-cerebellar atrophy, motor neuropathy, epilepsy or seizures, peripheral neuropathy, cerebral palsy, glaucoma, age related loss of neurons or neuronal connectivity and related deterioration of sensory, motor, reflect, or cognitive abilities. For example, the subject suffers from an injury caused by or associated with peripheral neuropathies and/or peripheral nerve damage associated with spinal cord injury. The peripheral neuropathy is diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy.

Alternatively, the subject suffers from a neurological injury resulting from a trauma, e.g., optic nerve trauma or spinal cord trauma. Or, the subject suffers from a neurological injury resulting from exposure to a toxin.

Administration of the compound or agent described herein is oral, subcutaneous, intravenous, intravitreal, intraorbital, parenteral, enteral and/or topical. Preferably, contacting is by ocular administration.

Optionally, the method includes further contacting the neuron with D-mannose, oncomodulin, transforming growth factor beta (TGF-β), IGF-1, nerve growth factor (NGF), brain-derived neurotrophic factor (BDNF), ciliary neurotrophic factor (CNTF), glial cell derived neurotrophic factor (GDNF), wnt, and/or a cyclic adenosine monophosphate (cAMP) activator, mammalian target of rapamycin (mTOR) activator, suppressor of cytokine signaling 3 (SOCS3) activator and B-cell lymphoma 2 (Bcl-2) activator. The cAMP activators are, e.g., non-hydrolyzable cAMP analogues, adenylate cyclase activators, calcium ionophores, phosphodiesterase inhibitors, specific phosphodiesterase IV inhibitors, beta2-adrenoreceptor inhibitors or vasoactive intestinal peptide.

The invention also provides a method of treating a disorder or condition in a subject associated with injury to a neuron(s) comprising administering a therapeutically effective amount of an agent that increases IGFBPL1 activity to the subject in an amount sufficient to promote nerve fiber outgrowth in the subject. The disorder or condition is, e.g., acute spinal cord damage, stroke, Huntington's disease, Parkinson's disease, Multiple Sclerosis, Alzheimer's disease, multiple system atrophy (MSA), spino-cerebellar atrophy, amyotrophic lateral sclersosis, motor neuronopathy, epilepsy or seizures, peripheral neuropthy, cerebral palsy, glaucoma, macular degeneration, photoreceptor dystrophy, age related macular degeneration, retinitis pigmentosa, retinal detachment, damage associated with laser therapy (including photodynamic therapy), surgical light-induced iatrogenic retinopathy, optic neuritis.

Also provided is a method of treating a neuronal injury in a subject by administering a therapeutically effective amount of agent to the subject sufficient to promote nerve fiber outgrowth or neuroregeneration in the subject. Administration of the compound or agent described herein is oral, subcutaneous, intravenous, intravitreal, intraorbital, intracameral, parenteral, enteral and/or topical. Preferably, contacting is by ocular administration.

The method optionally includes further administering an effective amount of D-mannose, a cAMP activator, oncomodulin, wnt, TGF-β, BDNF, GDNF, CNTF, and/or IGF-1 to the subject.

The agent is optionally administered in the absence of xanthine oxidase and/or in the absence of exogenous nerve growth factor (NGF), and/or in the absence of exogenous D-mannose, and/or in the absence of exogenous oncomodulin, and/or in the absence of exogenous TGF-B, and/or in the absence of IGF-1.

Also provided by the invention is a pharmaceutical composition comprising an agent that increases IGFBPL-1 activity and a pharmaceutically acceptable carrier. The composition may further include, e.g., D-mannose, oncomodulin, TGF-β, IGF-1 and/or a cAMP activator, and a pharmaceutically acceptable carrier. A cAMP modulator can include, e.g., non-hydrolyzable cAMP analogues, forskolin, adenylate cyclase activators, macrophage-derived factors that stimulate cAMP, macrophage activators, calcium ionophores, phosphodiesterase inhibitors, specific phosphodiesterase IV inhibitors, beta2-adrenoreceptor inhibitors or vasoactive intestinal peptide. If desired, the composition may further include one or more axogenic factors. Axogenic factors include, e.g., mannose, a mannose derivative, inosine, oncomodulin, and combinations thereof.

Also provided by the invention is a method of treating vision loss by identifying a subject characterized as suffering from or at risk of developing glaucoma or optic nerve degeneration/damage, and locally administering to an eye tissue a composition comprising an agent that increases IGFBPL-1 activity or levels.

In a further aspect, the invention provides a method of treating vision loss by identifying a subject characterized as suffering from or at risk of developing glaucoma or optic nerve degeneration/damage, and locally administering to an eye tissue a composition comprising IGFBPL-1 or an agonist thereof.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

Although the phrase "nucleic acid molecule" primarily refers to the physical nucleic acid and the phrase "nucleic acid sequence" refers to the linear list of nucleotides of the nucleic acid molecule, the two phrases can be used interchangeably.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to reduce or prevent optic nerve degeneration in a mammal. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

As shown in FIG. 1, this pattern of IGFBPL-1 expression inversely correlates with the loss of optic nerve regenerative capacity by retinal ganglion cells.

FIG. 2A is a western blot analysis of IGFBPL-1 expression. FIG. 2B is a qRG-PCR analysis of IGFBPL-1 and IGF-1 mRNA. The IGFBPL-1 protein (FIG. 2A) and mRNA (FIG. 2B) levels were measured using Western blot and quantitative RT-PCR, respectively. Note that IGFBPL-1 protein and mRNAs are highly expressed in E16 retinas, but are decreased in P0 and older retina.

FIG. 3A-FIG. 3B are a series of photomicrographs showing IGFBPL-1 promotes RGC neurite outgrowth in culture. FIG. 3A and FIG. 3B show RGC neurite outgrowth in the absence (FIG. 3A) and presence (FIG. 3B) of IGFBPL-1 promotes in RGC cell culture. Retinal ganglion cells (RGCs) isolated from P0 mice were cultured in the absence (control) and presence of IGFBPL-1 (IGFBPL-1) for 3 days and were immunolabeled with primary antibody against a RGC specific marker Tuj1 (red). Note that RGCs extend long neurite in IGFBPL-1-treated cultures as compared to control culture group.

FIG. 4 is a histogram showing quantification of RGC neurite outgrowth in culture in the presence of increasing amounts of IGFBPL-1. * P<0.01 compared to the control. IGFBPL-1 stimulates neurite outgrowth in RGC cultures isolated from P0 mouse pups.

FIGS. 5 (I) A and B and FIGS. 5 (II) A and B are western blots showing binding of IGFBP-1 with IGF-I using mouse recombinant IGFBPL-1 and IGF-1 (FIG. 5 (I)) and retina lysates (FIG. 5 (II)). The co-immuno-precipitation of IGFBPL-1 and IGF-1 demonstrates that IGFBPL-1 direct interacts with IGF-1.

FIGS. 6A and 6B are immunoflourescence images (FIG. 6A) and a bar chart (FIG. 6B) showing impairment of neurite outgrowth in cultured P0 RGC following knockdown of IGFBPL-1 by scramble shRNA and lentiviral shRNA.

FIGS. 7A-I are immunofluoresecence images showing that blockade of IGFI-1 signaling abolishes IGFBPL-1 induced axon growth in P0 RGC cultures. Specifically, the figure shows images of RGC axon morphology. P0 RGC cultures treated with IGFBPL-1, IGF-1 or both exhibited robust neurite outgrowth. Application of NBI-31772, a pan inhibitor that generally disrupts the binding of IGF-1 with its binding proteins, H1356 (inhibitor of IGF-1 binding with its receptor), or an IGF-1 neutralizing antibody abolishes the neurite growth effect of IGFBPL-1. The results show that IGFBPL-1 acts through IGF-1-mediated pathways to stimulate RGC neurite outgrowth.

FIG. 9A shows hippocampal neurons stained with beta III tubulan. FIG. 9B are histograms showing quantification of neurite outgrowth in control; and neurons exposed to IGFBPL-1; IGF-1; IGFBPL-1+IGF-1; IGFBPL-1+H1356; IGFBPL-1+Neut. Ab; IGFBPL-1+IGFI-1+Neut. Ab. Similar effects of the IGF-1 inhibitors were observed in cultured hippocampal neurons.

FIG. 11B-FIG. 11D are photographs of western blots of IGF-I, IGFBPL1 and IGF-IR in the developing mouse retina. FIG. 11E is a bar chart showing the quantification of IGF-I, IGFBPL1, IGFBP2 and IGFBP3 mRNA expression in the developing mouse retina, using quantitative RT-PCR. The data confirmed high expression of IGF-I, IGFBPL1 and IGFIR in the E16 retina but their expression is downregulated in the postnatal stage.

FIG. 12A shows representative photomicrographs of cultured P0 RGCs that were infected by lentiviral vector carrying scramble shRNA (a), IGF-I shRNA (b), and IGFBPL1 shRNA (c). All lentiviral constructs contained an EGFP reporter gene. FIG. 12B shows the quantification of neurite length in P0 RGC cultures that were treated with lentiviral vector carrying different shRNAs. *P<0.01 as compared to Scramble shRNA treated group (by two tailed student t-test). Note that knockdown of ether IGF-I or IGFBPL1 impaired RGC neurite outgrowth in culture, indicating the requirement of both signals for RGC axon extension.

FIG. 13A shows representative photomicrographs of cultured RGCs derived from P10 mice. Cells were treated with control, IGF-I, IGFBPL1 or both for 3 days and were immunostained with βIII-tubulin to reveal axons. FIG. 13B shows the quantification of axon length from cultured RGCs. Note that addition of IGF-I or IGFBPL1 alone does not promote neurite outgrowth, and both IGF-I and IGFBPL-1 are required to stimulate axon elongation in cultured RGCs derived from P10 mouse pups. FIG. 13C shows the quantification of RGC survival. Note that either IGF-I or IGFBPL1 affect the survival of RGCs derived from P10 mice. **P<0.01 as compared to controls by t-test.

FIG. 14A shows representative epifluorescence photomicrographs of cultured P0 RGCs under different treatments. Cells were immunostained with BIII-tubulin. FIG. 14B and FIG. 14C show the quantification of RGC neurite length (FIG. 14B) and cell survival (FIG. 14C). Note that administration of either IGF-I or IGFBPL1 promotes both neurite outgrowth and cell survival. **P<0.01, *P<0.05, NS: no significance, as compared to the control group by two tailed student t-test.

FIG. 15A shows representative photomicrographs of cultured P0 RGCs that were treated with IGF-I or IGFBPL1 in the presence or absence of various IGF-1 inhibitors or neutralizing antibodies. Cells were immunostained with BIII-tubulin. FIG. 15B shows the quantification of axon length in cultured RGCs. **P<0.01 as compared to the control group by t-test. Note that disruption of IGF-I signaling by administration of IGF-I neutralizing antibody, IGF-IR inhibitor or inhibitor of IGF-I and IGFBP binding abolishes the growth promoting activity of IGFBPL1, suggesting that the activity of IGFBPL1 requires the presence of IGF-I signaling.

DETAILED DESCRIPTION OF THE INVENTION

Figure 1:
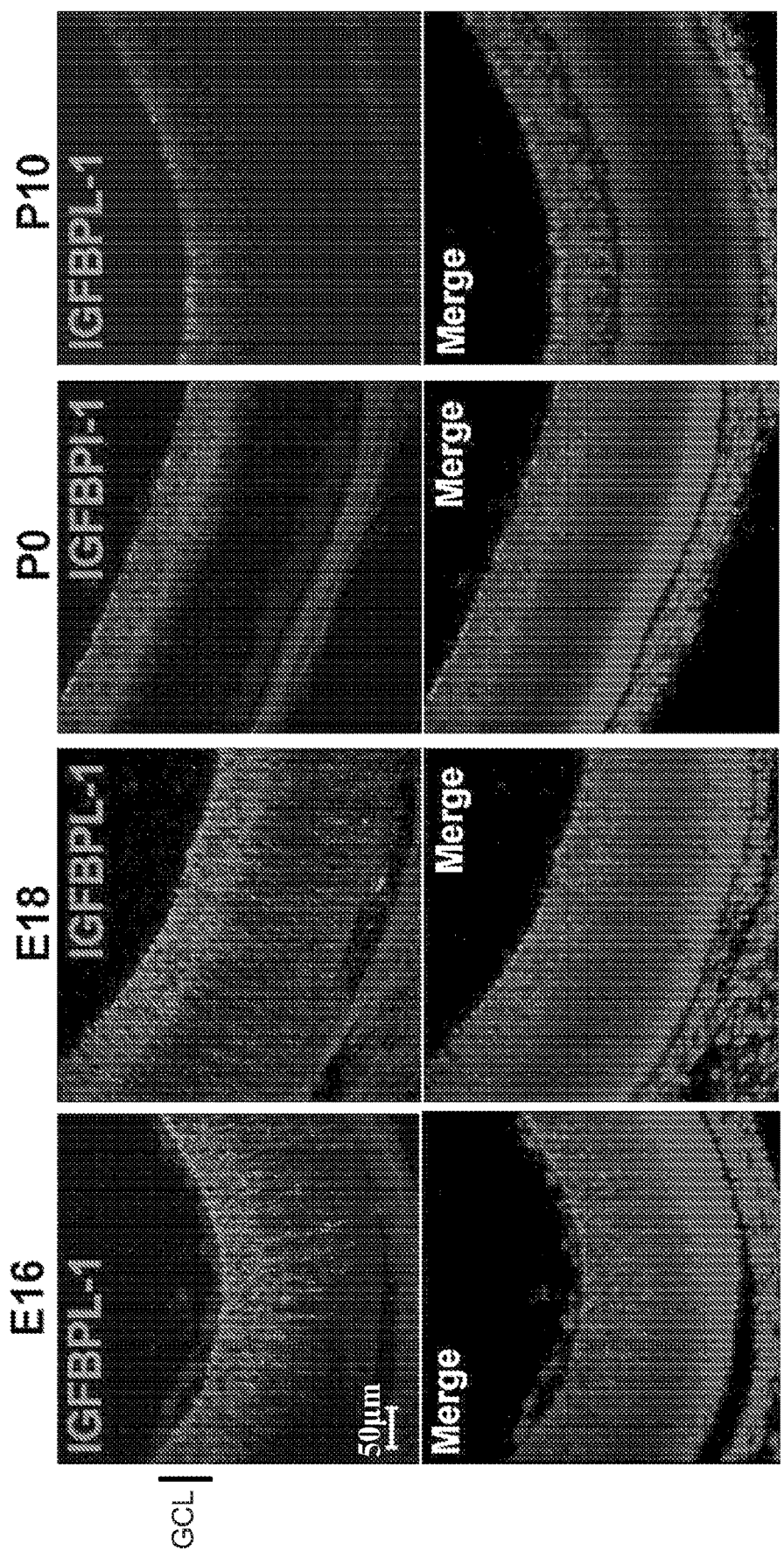
FIG. 1 is a series of photomicrographs showing immunodetection of IGFBPl-1 expression in the developing mouse retina. Transverse retinal sections taken from mice at embryonic day 16 (E16), E18 and postnatal day 0 (P0) and P10 were immunolabeled for IGFBPL-1 (red) and were counterstained with a nuclear marker DAPI (blue). Expression of IGFBPL-1 was detected in the ganglion cell layer (GCL) of mice, with highest expression E16 to E18. The level of IGFBPL-1 expression decreased drastically after postnatal day 0 (P0) and was absent in mature retinal ganglion cells.

Retinal ganglion cell death and optic nerve degeneration caused by trauma, ischemia and diseases is currently an irreversible process that eventually leads to blindness. A number of cell-autonomous factors, such as Bcl-2, cAMP (cyclic adenosine 3',5'-monophosphate) and CREB (cAMP response element-finding protein), PTEN (phosphatase and tensin homolog), suppressor of cytokine signaling 3 (SOCS3), KLF4 (Kruppel-ike factor 4—a negative regulator) and IGF-1 play roles in the developmental loss of RGC axon regeneration. However, manipulating Bcl-2 and/or other intracellular regulators of axon growth, even when simultaneously overcoming environmental inhibition, only partially restores the growth capacity of RGC axons, hence limiting neuroprotection and repair after injury. Described herein is the identification of additional axon growth regulators. The results demonstrate that IGFBPL-1 has potent efficacy in promoting RGC survival and axon regeneration post-natally, and serves as a key regulator on axon growth capacity during pre-natal development.

The invention is based on studies showing that expression of IGFBPL1 is restricted to the RGC layer in the retina with a transient high expression at E16-E18 and is largely downregulated postnatally. Addition of IGFBPL1 alone or together with IGF-I in P0 RGC cultures significantly promoted axonal extension. Knock down IGFBPL1 signaling abolishes axonal growth activity in RGCs without significantly altering the survival and number of RGCs. The results presented herein demonstrate a utility for IGFBPL1 as an important regulator of RGC axonal growth during retinal development, functioning by facilitating the IGF-I signaling pathway and to promote RGC axon growth, protection, regeneration and/or repair. As described herein, IGF-1 compositions, or compounds that increase the activity or stability of IGF-1, are useful for treating ocular conditions or disease such as glaucoma, optic nerve injury, as well as central nervous system (CNS) pathologies such as traumatic brain-related injury, spinal cord injury, multiple sclerosis, Alzheimer's disease, and Parkinson's disease. In some embodiments, administration of IGFBPL1 results in increased axonal growth in the eye, optic nerve regeneration, and/or improvement in vision.

Representative disease or conditions that benefit from this treatment include, e.g., neurodegenerative disorders in the brain and eye. Thus, the methods are used for neuroprotective and regenerative therapy for neural injury and neural development. Such disorders include optic nerve trauma, ischemia, optic neuritis, glaucoma, macular degeneration, retinitis pigmentosa; spinal cord injury, stroke, amyotrophic lateral sclerosis, Alzheimer's disease, Huntington's disease, Parkinson's disease.

In general, ocular, CNS, and PNS disorders or injuries are identified using methods known in the art. For example, a subject with Alzheimer's disease is identified by observing symptoms such as difficulty performing tasks that take some thought, but used to come easily, such as balancing a checkbook, playing complex games (such as bridge); learning new information or routines; getting lost on familiar routes; language problems, such as trouble finding the name of familiar objects; losing interest in things previously enjoyed; flat mood; misplacing items; personality changes and loss of social skills. Alzheimer's disease is also described in Dubois et al., 2007 Lancet Neurol, August; 6(8):734-46, incorporated herein by reference.

A subject with traumatic brain injury (TBI; e.g., blast-related TBI) is identified, e.g., by utilizing the Glasgow Coma Scale for Diagnosing Traumatic Brain Injury (i.e., evaluation of motor response, verbal response, and eye opening) and/or the Ranchos Los Amigos Scale for Diagnosing Traumatic Brain Injury (i.e., the varying levels of response and cognition). Each patient with TBI presents with different symptoms. Thus, the treatment for TBI varies based on the needs of the patient. Various treatments for traumatic brain injury include speech therapy, physical therapy, occupational therapy, and therapeutic recreation. TBI is also described in Kubal W S, 2012 Radiol Clin North Am, January; 50(1):15-41, incorporated herein by reference.

A subject with glaucoma is identified by, e.g., measuring intraocular pressure, determining the presence of optic nerve damage, performing a visual field test to determine if the visual field is affected, and by measuring corneal thickness. To distinguish between open-angle glaucoma and angle-closure glaucoma, a physician may use a technique called gonioscopy in which a special lens is placed on the eye to inspect the drainage angle. Another test, tonography, measures how quickly fluid drains from the eye. Glaucoma is also described in Tarride et al., 2011 Can J Ophthalmol, February; 46(1):89-90, incorporated herein by reference.

A subject with Huntington disease is identified by observing various symptoms (e.g., dementia, abnormal movements, abnormal reflexes, "prancing" and wide walk, and hesitant speech or poor enunciation), and is confirmed with a cranial computed tomography (CT) scan, a cranial magnetic resonance imaging scan, or a positron emission tomography scan of the brain. Huntington disease is also described in Novak et al., 2011 Int Rev Neurobiol, 98:297-323, incorporated herein by reference.

Any agent that specifically increases the amount or activity of IGFBPL-1 polypeptide can be used in the invention. Accordingly, in some cases, IGFBPL-1 polypeptide is used. Alternatively, a nucleic acid encoding an IGFBPL-1 polypeptide is used. The agent stabilizes an IGFPL-1 polypeptide or nucleic acid, or alternatively stabilizes a complex of a IGFBPL-1 and IGF-1 polypeptide.

The agent is provided in composition as, e.g., a solid, a paste, an ointment, gel, a liquid, an aerosol, a mist, a polymer, a film, an emulsion, or a suspension. The composition is optionally administered topically. Preferably, the methods described herein do not include systemic administration or substantial dissemination to non-ocular tissue.

In some cases, the composition further includes a compound selected from the group consisting of a physiological acceptable salt, poloxamer analogs with carbopol, carbopol/HPMC, carbopol-methyl cellulose, a mucolytic agent, carboxymethylcellulose (CMC), hyaluronic acid, cyclodextrin, and petroleum. An exemplary mucolytic agent is N-acetyl cysteine. Preferably, the composition further includes carboxymethylcellulose (CMC).

Alternatively, or in addition, a composition of the above methods includes oligonucleotide containing a fragment of IGFBPL-1 mRNA or cDNA, a morpholino antisense oligonucleotide, microRNA (miRNA), short hairpin RNA (shRNA), or short interfering RNA (siRNA) of a IGFBPL1 nucleic acid.

The sequences of full length human IGFBPL-1 and IGF-1 are provided below. However, the invention also comprises polypeptides and nucleic acid fragments, so long as they exhibit the desired biological activity (i.e., neuronal outgrowth promoting activity) of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The sequence of IGFBPL-1 (Insulin-like growth factor-binding protein-like 1 precursor sequence [*Homo sapiens*]) is provided below (SEQ ID NO: 1; Genbank Accession Number NM_001007563.1 (GI:56090547), incorporated herein by reference). The starting "atg" is underlined.

```
   1 ccgccgctgt cccggagcaa gccatgccgc gcttgtctct gctcttgccg ctgctgcttc
  61 tgctgctgct gccgctgctg ccgccgctgt ccccgagcct tgggatccgc gacgtgggcg
 121 gccggcgccc caagtgtggt ccgtgccggc cagagggctg cccggcgcct gcgccctgcc
 181 cggcgccggg atctcggcg ctcgacgagt gcggctgctg cgcccgctgc ctgggagccg
 241 agggcgcgag ctgcggggc cgcgccggcg ggcgctgtgg ccccggcctg gtatgcgcga
 301 gccaggccgc tggggcagcg cccgagggca ccgggctctg cgtgtgcgcg cagcgcggca
 361 ccgtctgcgg ctccgacggt cgctcgtacc ccagcgtctg cgcgctgcgc ctgcgcgctc
 421 ggcacacgcc ccgcgcgcac cccggtcacc tgcacaaggc gcgcgacggc ccttgcgagt
 481 tcgctcctgt ggtcgtcgtt cctccccgaa gtgttcacaa cgtcaccggg gcgcaggtgg
 541 gcctgtcctg tgaagtgagg gctgtgccta ccccagtcat cacgtggaga aaggtcacga
 601 agtcccctga gggcacccaa gcactggagg agctgcctgg ggaccatgtc aatatagctg
 661 tccaagtgcg aggggggcct tctgaccatg aggccacggc ctggatttg atcaaccccc
 721 tgcgaaagga ggatgagggt gtgtaccagt gccatgcagc caacatggtg ggagaggctg
 781 agtcccacag cacagtgacg gttctagatc tgagtaaata caggagcttc cacttcccag
 841 ctcccgatga ccgcatgtga tggagaaatg gtcttagaaa cattgatcat gggatgatgg
 901 aaaagtcaaa taacggatct ttgtgcttca tgaagagttg gaaaacctgt gtgtgtagat
 961 gaccccttt gtgtgttttt aaaaattaga tgcaaactag atctgtatgc agatgtagtt
1021 tttagcaggg caaacagtga gaaacggatt tgcatgtggc ttttttatac ttttgaaatg
1081 aattgttcca tga
```

The amino acid sequence of a polypeptide encoded by human IGFBPL-1 nucleic acid is provided below (SEQ ID NO: 2; GenBank Accession Number NP_001007564.1 (GI: 56090548), incorporated herein by reference).

MPRLSLLLPLLLLLLLPLLPPLSPSLGIRDVGGRRPKCGPCRPEGCPAP
APCPAPGISALDECGCCARCLGAEGASCGGRAGGRCGPGLVCASQAAGA
APEGTGLCVCAQRGTVCGSDGRSYPSVCALRLRARHTPRAHPGHLHKAR
DGPCEFAPVVVVPPRSVHNVTGAQVGLSCEVRAVPTPVITWRKVTKSPE
GTQALEELPGDHVNIAVQVRGGPSDHEATAWILINPLRKEDEGVYQCHA
ANMVGEAESHSTVTVLDLSKYRSFHFPAPDDRM

The nucleic acid sequence of human Insulin Growth Factor-1 (IGF-1) is provided below (SEQ ID NO: 3; GenBank Accession Number X00173.1 (GI:33015), incorporated herein by reference). The starting "atg" is underlined.

```
  1 cttcagaagc aatgggaaaa atcagcagtc ttccaaccca attatttaag tgctgctttt
 61 gtgatttctt gaaggtgaag atgcacacca tgtcctcctc gcatctcttc tacctggcgc
121 tgtgcctgct caccttcacc agctctgcca cggctggacc ggagacgctc tgcggggctg
181 agctggtgga tgctcttcag ttcgtgtgtg agacagggg cttttatttc aacaagccca
241 cagggtatgg ctccagcagt cggagggcgc ctcagacagg tatcgtggat gagtgctgct
301 tccggagctg tgatctaagg aggctggaga tgtattgcgc accctcaag cctgccaagt
361 cagctcgctc tgtccgtgcc cagcgccaca ccgacatgcc caagacccag aaggaagtac
421 atttgaagaa cgcaagtaga gggagtgcag gaaacaagaa ctacaggatg taggaagacc
481 ctcctgagga gtgaagagtg acatgccacc gcaggatcct tgctctgca cgagttacct
541 gttaaacttt ggaacaccta ccaaaaaata gtttgataa catttaaaag atgggcgttt
601 cccccaatga aatacacaag taaacattcc aacattgtct ttaggagtga tttgcacctt
661 gcaaaaatgg tcctggagtt ggtagattgc tgttgatctt ttatcaataa tgttctatag
721 aaaag
```

The amino acid sequence of a human IGF-1 polypeptide according to the invention is below: (SEQ ID NO: 4; GenBank Accession Number CAA24998.1 (GI:33016), incorporated herein by reference).

MGKISSLPTQLFKCCFCDFLKVKMHTMSSSHLFYLALCLLTFTSSATAG

PETLCGAELVDALQFVCGDRGFYFNKPTGYGSSSRRAPQTGIVDECCFR

SCDLRRLEMYCAPLKPAKSARSVRAQRHTDMPKTQKEVHLKNASRGSAG

NKNYRM

The contacting of a neuronal cell with the agent that increases IGFBPL1 activity or levels to the neuron occurs either in vivo or in vitro. The neuron is contacted with an agent that increases IGFBPL1 activity or levels under conditions appropriate for growth and/or maintenance of the neuron (e.g. the environment of the neuron provides the appropriate nutrients, temperature, etc.). An effective amount is an amount which delivers sufficient an agent that increases IGFBPL1 activity or levels to the target neuron(s), neural progenitor cells, or stem cells to produce a detectable, amount of nerve fiber outgrowth or generate new neurons which extend new nerve fibers. Detection can be by physical examination of the neuron(s) or by functional analysis as described herein.

Contacting in vitro is often carried out by including the agent in the media in which the cells or tissue are grown. Contacting in vivo is generally achieved by administration of an agent that increases IGFBPL-1 activity or levels to a subject in which the target neuron(s) or cell(s) resides. One of skill in the art will recognize that the effective amount for in vivo contact may require a higher dose of administration to result in a sufficient amount of an agent that increases IGFBPL-1 activity or levels reaching the target neuron.

As the term is used herein, a "target neuron" is a neuron in which outgrowth is desired. The agent that increases IGFBPL-1 activity or levels is directed toward, and ultimately contacts the target neuron, thereby producing outgrowth.

As used herein, the term "nerve fiber outgrowth" refers to the process by which axons and/or dendrites grow out of a neuron. The outgrowth can result in a totally new axon, increased growth of an already extended axon, or the repair of a partially damaged axon. Outgrowth is typically evidenced by extension of an axonal process of at least 2 cell diameters in length.

As used herein, the language "inducing the outgrowth of nerve fibers" is intended to include the capacity to stimulate outgrowth of nerves to various levels, e.g., to levels which allow for the treatment of targeted neuronal injuries.

Types of Neurons

The neurons are optionally mammalian neurons, for example, neurons from a primate (e.g., human neurons). Other examples of mammalian neurons include those from animals typically kept as pets (e.g., dogs, cats, birds, horses), farm animals (e.g., goats, pigs, cows, horses, sheep, poultry fowl), and exotic animals or zoo animals. Preferably, the neuron is not a rabbit neuron.

One or more central nervous system (CNS) neurons are optionally contacted with an agent that increases IGFBPL-1 activity or levels. In some cases, the CNS neuron is unresponsive to nerve growth factor (NGF). In some cases, the term CNS neuron is not intended to include support or protection cells such as astrocytes, oligodentrocytes, microglia, ependyma and the like, nor is it intended to include peripheral nervous system (e.g., somatic, autonomic, sympathetic or parasympathetic nervous system) neurons. Although, as described herein, these cells are also contacted with an agent that increases IGFBPL-1 activity or levels.

Alternatively, one or more peripheral nervous system neurons are contacted with an agent that increases IGFBPL-1 activity or levels. As used herein, the term "PNS (peripheral nervous system) neurons" is intended to include the neurons commonly understood as categorized in the peripheral nervous system, including sensory neurons and motor neurons. In some cases, the term "PNS neuron" is not intended to include support or protection cells such as Schwann cells and macrophages, nor is it intended to include CNS nervous system neurons. Although, as described herein, these cells are also contacted with an agent that increases IGFBPL-1 activity or levels.

In some examples, the neuron which is contacted is injured prior to the contact (herein referred to as an "injured neuron"). For example, the neuron is an optic nerve neuron or a retinal neuron.

Treatment Methods

Methods for treatment/treating of a subject with an injured neuron is carried out by administration of an agent that increases IGFBPL-1 activity or levels to the subject with the injured or diseased neuron. Administration is performed to promote contact of an effective amount of the administered an agent that increases IGFBPL-1 activity or levels to the injured neuron within the subject. A therapeutically effective amount of an agent that increases IGFBPL-1 activity or levels or pharmaceutical composition containing an agent that increases IGFBPL-1 activity or levels is administered to the subject. The method may further comprise selecting a subject in need of such treatment (e.g., identification of a damaged nerve, (e.g., CNS and/or PNS). The injury may occur by one or more means described herein. Optionally, administration occurs following neuronal injury in the subject, not prior to, or concurrent with injury.

As used herein, the term "subject" is intended to include animals susceptible to neuronal (e.g., CNS or PNS) injuries, mammals, such as primates (e.g. human). Other examples of subjects include animals typically kept as pets (e.g., dogs, cats, birds, horses), farm animals (e.g., goats, pigs, cows, horses, sheep, poultry fowl) and exotic animals or zoo animals. Preferably, the subject is not a rabbit.

Another aspect of the invention relates to method for treatment/treating a disease, disorder or condition associated with damage to a neuron or reduced neuronal outgrowth of a neuron, by administration of an agent that increases IGFBPL-1 activity or levels to a subject with such a disease, disorder or condition. As used herein, the term "associated with" injury to a neuron, when used in conjunction with disease, disorder or condition, refers to the damage or injury to the neuron resulting from or causing the disease symptoms. Such disorders or conditions are generally known in the art, with representative diseases, disorders and conditions so associated being described herein. The subject may be at risk for such a disease, disorder or conditions or suspected of being in the early stages of development. Prevention of the development or progression of such a disease, disorder or condition by the methods described herein is also envisioned. For treatment or prevention, a therapeutically effective amount of an agent that increases IGFBPL-1 activity or levels is administered. An agent that increases IGFBPL-1 activity or levels can be administered in the presence of one or more exogenous factors (e.g., NGF, BDNF, GDNF, CNTF, IGF-1, sonic hedgehog, wnt, a hexose or hexose derivative, oncomodulin, TGF-β, inosine, other axogenic factors, a cAMP activator) described herein. For instance, they can be co-administered, or administered separately. The agent that increases IGFBPL-1 activity or levels is optionally administered in the absence of one or more exogenous factors described herein (e.g., NGF, BDNF, a hexose or hexose derivative, oncomodulin, TGF-β, inosine, other axogenic factors, a cAMP activator).

The method may further comprise selecting a subject in need of treatment or prevention of nerve damage (CNS and/or PNS). Such selection may involve identification within a subject of nerve damage and/or identification of a risk for the development of nerve damage in the subject.

In general, ocular, CNS, and PNS disorders or injuries are identified using methods known in the art. For example, a subject with Alzheimer's disease is identified by observing symptoms such as difficulty performing tasks that take some thought, but used to come easily, such as balancing a checkbook, playing complex games (such as bridge); learning new information or routines; getting lost on familiar routes; language problems, such as trouble finding the name of familiar objects; losing interest in things previously enjoyed; flat mood; misplacing items; personality changes and loss of social skills. Alzheimer's disease is also described in Dubois et al., 2007 Lancet Neurol, August; 6(8):734-46, incorporated herein by reference.

A subject with traumatic brain injury (TBI; e.g., blast-related TBI) is identified, e.g., by utilizing the Glasgow Coma Scale for Diagnosing Traumatic Brain Injury (i.e., evaluation of motor response, verbal response, and eye opening) and/or the Ranchos Los Amigos Scale for Diagnosing Traumatic Brain Injury (i.e., the varying levels of response and cognition). Each patient with TBI presents with different symptoms. Thus, the treatment for TBI varies based on the needs of the patient. Various treatments for traumatic brain injury include speech therapy, physical therapy, occupational therapy, and therapeutic recreation. TBI is also described in Kubal W S, 2012 Radiol Clin North Am, January; 50(1):15-41, incorporated herein by reference.

A subject with glaucoma is identified by, e.g., measuring intraocular pressure, determining the presence of optic nerve damage, performing a visual field test to determine if the visual field is affected, and by measuring corneal thickness. To distinguish between open-angle glaucoma and angle-closure glaucoma, a physician may use a technique called gonioscopy in which a special lens is placed on the eye to inspect the drainage angle. Another test, tonography, measures how quickly fluid drains from the eye. Glaucoma is also described in Tarride et al., 2011 Can J Ophthalmol, February; 46(1):89-90, incorporated herein by reference.

A subject with Huntington disease is identified by observing various symptoms (e.g., dementia, abnormal movements, abnormal reflexes, "prancing" and wide walk, and hesitant speech or poor enunciation), and is confirmed with a cranial computed tomography (CT) scan, a cranial magnetic resonance imaging scan, or a positron emission tomography scan of the brain. Huntington disease is also described in Novak et al., 2011 Int Rev Neurobiol, 98:297-323, incorporated herein by reference.

The methods described herein may further comprise the step of detecting a resultant neuronal outgrowth following treatment or in the course of treatment. For in vitro applications, the therapeutic effect of neural regeneration can be detected by any routinely used method such as a neurite outgrowth assay. For in vivo applications, neuronal outgrowth can be detected by detecting neural regeneration. Such regeneration can be detected using imaging methodologies such as confocal microscopy and MRI. More commonly, neural regeneration will be detected inferentially by neurological examination showing improvement in the patient's neural function or vision. The detecting step may occur at any time point after initiation of an agent that increases IGFBPL-1 activity or levels administration, e.g., at least one day, one week, one month, three months, six months, after initiation of treatment. In some cases, the detecting step will comprise an initial neurological examination and a subsequent neurological examination conducted at least one day, week, or month after the initial exam. Improved neurological function at the subsequent exam compared to the initial exam indicates resultant neural regeneration. The specific detection and/or examination methods used will usually be based on the prevailing standard of medical care for the particular type of neural damage being evaluated (i.e. trauma, neurodegeneration, etc.).

Administration of an agent that increases IGFBPL-1 activity or levels to a subject, alone or in combinations described herein is to be made under conditions effective to stimulate nerve regeneration at the site of the injury and/or under conditions effective to at least partially restore nerve function (e.g., through an injured spinal cord). Restoration of nerve function can be evidenced by restoration of nerve impulse conduction, a detectable increase in conduction action potentials, observation of anatomical continuity, restoration of more than one spinal root level, an increase in behavior or sensitivity, or a combination thereof. Administration is by a method which results in contacting the administered factors with the site of injury to thereby promote nerve regeneration (complete or partial).

Administering the formulation to the eye can involve cell transplantation, nanoparticle carriers, eye drops, salves, or implantable devices, depending on the precise nature of the formulation and the desired outcome of the administration. Specifically, a composition of the invention is delivered directly to the eye, (e.g., slow release devices such as pharmaceutical drug delivery sponges implanted in the cul-de-sac or implanted adjacent to the sclera or within the eye), using techniques well known by those of ordinary skill in the art. It is further contemplated that a polypeptide as disclosed herein is formulated in intraocular inserts or implantable devices. The ophthalmic formulations of the invention are administered in any form suitable for ocular drug administration, e.g., dosage forms suitable for topical administration, a solution or suspension for administration as eye drops or eye washes, ointment, gel, liposomal dispersion, colloidal microparticle suspension, or the like, or in an ocular insert such as a disc, and/or an optionally biodegradable controlled release polymeric matrix. The ocular insert is implanted in the conjunctiva, sclera, pars plana, anterior segment, or posterior segment of the eye. Implants provide for controlled release of the formulation to the surface, typically sustained release over an extended time period. Additionally, in a preferred embodiment, the formulation is entirely composed of components that are naturally occurring and/or as GRAS ("Generally Regarded as Safe") by the U.S. Food and Drug Administration.

Injuries, Diseases and Disorders

The injury of the neuron for treatment can be acute or chronic. An injury can be complete severing, or partial severing of the nerve or axon tract, or crushing or compression injury to the neuron or nerve fibers. For example, an injury to a nerve or neuron directly impairs the normal functioning of the neuron. Alternatively, the injury to the nerve fiber or neuron indirectly impairs the normal functioning of the neuron. The injury to a nerve fiber or neuron can result from an acute or traumatic event, chronic event, pressure build-up, chronic neurodegeneration. Injury to a subject often results in injury to a nerve fiber or neuron. Causes of neuronal injury include, without limitation, disease and/or infection, ischemia, anoxia, hypoglycemia, contusion, laceration, tumor, blast or shedding force, laser, trauma to the brain or spinal cord (such as caused by acute spinal cord damage or stroke), damage by exogenous chemical agents (e.g., exposure to a toxin), and combinations thereof.

As used herein, the term "stroke" is art recognized and is intended to include sudden diminution or loss of consciousness, sensation, and voluntary motion caused by rapture or obstruction (e.g., by a blood clot) of an artery of the brain. A spinal cord injury may be a complete severing of the spinal cord, a partial severing of the spinal cord, or a crushing or compression injury of the spinal cord.

The neuronal injury may also be associated with peripheral neuropathies including, but not limited to, the following: diabetic neuropathies, virus-associated neuropathies, including acquired immunodeficiency syndrome (AIDS) related neuropathy, infectious mononucleosis with polyneuritis, viral hepatitis with polyneuritis; Guillian-Barre syndrome; botulism-related neuropathy; toxic polyneuropathies including lead and alcohol-related neuropathies; nutritional neuropathies including subacute combined degeneration; angiopathic neuropathies including neuropathies associated with systemic lupus erythematosis; sarcoid-associated neuropathy; carcinomatous neuropathy; compression neuropathy (e.g. carpal tunnel syndrome) and hereditary neuropathies, such as Charcot-Marie-Tooth disease, peripheral nerve damage associated with spinal cord injury can also be treated with the present method.

Peripheral nerves such as dorsal root ganglia, otherwise known as spinal ganglia, are known to extend down the spinal column. These nerves can be injured as a result of spinal injury. Such peripheral nerve damage associated with spinal cord injury can also benefit from neuron axonal outgrowth produced by contact with an agent that increases IGFBPL-1 activity or levels. As such, the present invention relates to methods of treatment of such an injury, the method comprising administering an agent that increases IGFBPL-1 activity or levels to an individual in need thereof, to result in contact of the injured neuron with an effective amount of an agent that increases IGFBPL-1 activity or levels, to promote neuronal outgrowth.

Diseases, disorders, or conditions described herein as associated with injury to a neuron(s) can be treated in a subject by therapeutic administration of an agent that increases IGFBPL-1 activity or levels. As such, aspects of the invention relate to methods of treating an individual for such diseases, disorders or conditions, described herein, by the methods herein described. Diseases, disorders, or conditions associated with injury to a neuron(s) disorders or conditions in a subject, include, without limitation, damage to retinal ganglion cells; traumatic brain injury; stroke related injury; a cerebral aneurism related injury: a spinal cord injury, including monoplegia, diplegia, paraplegia, hemiplegia and quadriplegia; a neuroproliferative disorder or neuropathic pain syndrome.

Neuronal injury may also result from neurodegeneration which, for example, can be caused by or associated with neurotoxicity or a neurological disease, disorder or condition. Such disease or disorder includes, without limitation, Huntington's disease, Parkinson's disease, Multiple Sclerosis, Alzheimer's disease, multiple system atrophy (MSA), spinocerebellar atrophy, motor neuronopathy, epilepsy or seizures, peripheral neuropathy, cerebral palsy, glaucoma (e.g., angle closure or open angle), age related loss of neurons or neuronal connectivity and related deterioration of sensory, motor, reflect, or cognitive abilities. Disease which are inflammatory and/or autoimmune disease can also cause or be indicated/associated with neuronal degeneration from which such neuronal injury can arise. Injury to optic nerve neurons or retinal neurons may occur from the above listed causes. Injury to the optic nerve may further be the result of branch and central vein/artery occlusion, trauma, edema, angle-closure glaucoma, open-angle glaucoma. Retinal neurons may be injured by macular degeneration, age related macular degeneration, retinitis pigmentosa, retinal detachments, damage associated with laser therapy, and surgical light-induced iatrogenic retinopathy.

In some instances, damage to the neuron may be evidenced by loss of function or the presence of physical damage, e.g., visible nerve damage such as a break in an extension (axon or dendrite) or another form of lesion. Subjects at risk for developing such neuronal damage can also be so treated by the methods described herein.

Other Agents

The agent that increases IGFBPL-1 activity or levels can be contacted to the injured neuron(s) in combination with, or prior or subsequent to, other treatment regimes. One such treatment regimen is the use of anti-inflammatory agents such as methylprednisolone.

An agent that increases IGFBPL-1 activity or levels can further be contacted in combination with other axogenic factors, such as inosine, hexose or hexose derivatives, oncomodulin, nerve growth factor (NGF), brain-derived neurotrophic factor (BDNF), ciliary neurotrophic factor (CNTF). It can also be contacted/administered in combination with a cAMP activator. The term "hexose derivative" refers to a hexose molecule that has one or more residues (e.g., esters, ethers, amino groups, amido groups, phosphate groups, sulphate groups, carboxyl groups, carboxy-alkyl groups, and combinations thereof) covalently or ionically attached to one or more of the molecules hydroxyl groups and able to produce a neurosalutary effect, as described in US Patent Application 20050256059. Hexoses include mannose (D and L isomers), glucose, glucose-6-phosphate, aminomannose, mannose-6-phosphate (Phosporic acid mano-(3,4,5,6-tetrahydroxy-tetrahydro-pyran-2-ylmethy) ester). While not wishing to be bound by a particular theory, it is believed that the cAMP and/or and axogenic factors may potentiate the activity of an agent that increases IGFBPL-1 activity or levels. Preferably, the cAMP activator is non-hydrolyzable cAMP analogue, forskolin, adenylate cyclase activators, calcium ionophores, membrane depolarization, phosphodiesterase inhibitors, specific phosphodiesterase IV inhibitors, beta2-adrenoreceptor inhibitors or vasoactive intestinal peptide, and combinations thereof.

Administration of an agent that increases IGFBPL-1 activity or levels to a subject, alone or in combinations described herein is to be made under conditions effective to stimulate nerve regeneration at the site of the injury and/or under conditions effective to at least partially restore nerve function through the injured spinal cord. Restoration of nerve function can be evidenced by restoration of nerve impulse conduction, a detectable increase in conduction action potentials, observation of anatomical continuity, restoration of more than one spinal root level, an increase in behavior or sensitivity, or a combination thereof. Administration is by a method which results in contacting the administered factors with the site of injury to thereby promote nerve regeneration (complete or partial).

In one embodiment, an agent that increases IGFBPL-1 activity or levels is not co-administered or administered concurrently with xanthine oxidase, or any other oxidizing method to generate reactive 02.

Pharmaceutically Acceptable Compositions

The agent that increases IGFBPL-1 activity or levels which is administered in vivo is optionally in a pharmaceutical composition or solution. The pharmaceutical composition or solution can further include one or more other exogenous agents (e.g., one or more axogenic factors, and/or cAMP activators) described herein as administered with or contacted in the presence of an agent that increases IGFBPL-1 activity or levels. The pharmaceutical composition or solutions may optionally, be specifically formulated to exclude one or more such other agents. The pharmaceutical composition can optionally be formulated to exclude xanthine oxidase, or any other oxidizing method to generate reactive oxygen. In some cases, the pharmaceutical composition consists essentially of an agent that increases IGFBPL-1 activity or levels and a pharmaceutically acceptable carrier. By the term "consists or consisting essentially of" is meant that the pharmaceutical composition does not contain any other active agents (e.g., modulators of neuronal growth such as, for example, NGF)).

In one aspect, the pharmaceutical composition of the invention can be provided as a packaged formulation. The packaged formulation may include a pharmaceutical composition of the invention in a container and printed instructions for administration of the composition for treating a subject having a neuronal injury, and/or disease, disorder or condition associated with an injury neurons, as described herein.

Pharmaceutical compositions are considered pharmaceutically acceptable for administration to a living organism. For example, they are sterile, the appropriate pH, and ionic strength, for administration. They generally contain an agent that increases IGFBPL-1 activity or levels formulated in a composition within/in combination with a pharmaceutically acceptable carrier, also known in the art as excipients.

The pharmaceutically acceptable carrier is formulated such that it facilitates delivery of the active ingredient (e.g., an agent that increases IGFBPL-1 activity or levels) to the target site. Such a carrier is suitable for administration and delivery to the target neuron. The pharmaceutically acceptable carrier will depend upon the location of the target neuron and the route of administration. For example, a typical carrier for intravenous administration of an agent is saline. The term "pharmaceutically acceptable carrier" includes, without limitation, any and all solvents, dispersion media, coatings, antibacterial and anti fungal agents, isotonic and absorption delaying agents, and the like that are physiologically compatible. For example, the carrier can be suitable for injection into the cerebrospinal fluid. The pharmaceutical composition can further be designed to provide protection of the agent that increases IGFBPL-1 activity or levels from unnecessary dispersion or degradation. The pharmaceutical composition may also contain additional ingredients such as stabilizers and disintegrants. Appropriate carriers and pharmaceutical compositions will be determined by the skilled practitioner. In some cases, the pharmaceutical composition is easily suspended in aqueous vehicles and introduced through conventional hypodermic needles or using infusion pumps.

Prior to introduction, the composition can be sterilized with, preferably, gamma radiation or electron beam sterilization, described in U.S. Pat. No. 436,742 the contents of which are incorporated herein by reference.

Additional examples of carriers are synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. Optionally, the pharmaceutically acceptable carrier comprises a polymeric matrix.

The terms "polymer" or "polymeric" are art-recognized and include a structural framework comprised of repeating monomer units which is capable of delivering an agent that increases IGFBPL-1 activity or levels or analog thereof such that treatment of a targeted condition, e.g., a CNS injury, occurs. The terms also include co-polymers and homopolymers e.g., synthetic or naturally occurring. Linear polymers, branched polymers, and cross-linked polymers are also meant to be included.

For example, polymeric materials suitable for forming the pharmaceutical composition employed in the present invention, include naturally derived polymers such as albumin, alginate, cellulose derivatives, collagen, fibrin, gelatin, and polysacchanides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of an agent that increases IGFBPL-1 activity or levels release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandler. S. R.; Karo, W. Polymer Syntheses; Harcourt Brace: Boston. 1994; Shalaby, W.; Ikada, Y.; Langer, R.: Williams, J. Polymers of Biological and Biomedical Significance (ACS Symposium Series 540; American Chemical Society: Washington, D.C. 1994). Polymers can be designed to be flexible; the distance between the bioactive side-chains and the length of a linker between the polymer backbone and the group can be controlled. Other suitable polymers and methods for their preparation are described in U.S. Pat. Nos. 5,455,044 and 5,576,018, the contents of which are incorporated herein by reference.

The polymeric formulations are preferably formed by dispersion of an agent that increases IGFBPL-1 activity or levels within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and an agent that increases IGFBPL-1 activity or levels, types of solvent used, and reaction times.

The agent that increases IGFBPL-1 activity or levels can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structures of the two. In one aspect of the present invention, the mean average diameter is less than about 45 µm, preferably less than 20 µm, and more preferably between about 0.1 and 10 µm.

The pharmaceutical composition optionally comprises lipid-based formulations. Any of the known lipid-based drug delivery systems can be used in the practice of the invention. For instance, multivesicular liposomes (MVL), multilamellar liposomes (also known as multilamellar vesicles or "MLV"). unilamellar liposomes, including small unilamellar liposomes (also known as unilamellar vesicles or "SUV") and large unilamellar liposomes (also known as large unilamellar vesicles or "LUV"), can all be used so long as a sustained releaserate of the encapsulated an agent that increases IGFBPL-1 activity or levels or analogue thereof can be established. In one embodiment, the lipid-based formulation can be a multivesicular liposome system. Methods of making controlled release multivesicular liposome drug delivery systems is described in PCT Application Serial Nos. US96/11642, US94/12957 and US94/04490, the contents of which are incorporated herein by reference. The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used. In preparing lipid-based vesicles containing an agent that increases IGFBPL-1 activity or levels, such variables as the efficiency of an agent that increases IGFBPL-1 activity or levels encapsulation, lability of an agent that increases IGFBPL-1 activity or levels, homogeneity and size of the resulting population of vesicles, an agent that increases IGFBPL-1 activity or levels-to-lipid ratio, permeability, instability of the preparation, and pharmaceutical acceptability of the formulation should be considered (see Szoka, et al., Annual Reviews of Biophysics and Bioengineering, 9:467, 1980; Deamer, et al., in Liposomes, Marcel Dekker, New York, 1983, 27; and Hope, et al., Chem. Phys. Lipids, 40:89, 1986, the contents of which are incorporated herein by reference). The pharmaceutical composition optionally provides sustained delivery, e.g., "slow release" of an agent that increases IGFBPL-1 activity or levels to a subject for at least one, two, three, or four weeks after the pharmaceutical composition is administered to the subject.

As used herein, the term "sustained delivery" is intended to include continual delivery of an agent that increases IGFBPL-1 activity or levels or analogue thereof in vivo over a period of time following administration, preferably at least several days, a week or several weeks. Sustained delivery of an agent that increases IGFBPL-1 activity or levels can be demonstrated by, for example, the continued therapeutic effect of an agent that increases IGFBPL-1 activity or levels over time (e.g., by continued outgrowth of neurons over time). Alternatively, sustained delivery of an agent that increases IGFBPL-1 activity or levels may be demonstrated by detecting the presence of an agent that increases IGFBPL-1 activity or levels in vivo over time.

In one embodiment, the pharmaceutical composition provides sustained delivery of an agent that increases IGFBPL-1 activity or levels or analogue thereof to a subject for less than 30 days after an agent that increases IGFBPL-1 activity or levels or analogue thereof is administered to the subject. For example, the pharmaceutical composition, e.g., "slow release" formulation, can provide sustained delivery of an agent that increases IGFBPL-1 activity or levels to a subject for one, two, three or four weeks after an agent that increases IGFBPL-1 activity or levels is administered to the subject. Alternatively, the pharmaceutically composition may provide sustained delivery of an agent that increases IGFBPL-1 activity or levels to a subject for more than 30 days after an agent that increases IGFBPL-1 activity or levels is administered to the subject.

Administration

Administration of an agent that increases IGFBPL-1 activity or levels to a subject, (e.g., in a pharmaceutical composition, with or without an additional axogenic factor described herein) optionally results in an agent that increases IGFBPL-1 activity or levels directly contacting a neuron in need of regeneration. The agent that increases IGFBPL-1 activity or levels and/or one or more of the factors optionally does not directly contact the neuron, but contacts the surrounding cells. Combinations of different forms of contacting with the various factors described herein are also envisioned.

Administration of a therapeutic amount of the compositions described herein is intended to produce a neurosalutary effect. The term "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. For example, examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; or reversing age-related loss of cholinergic innervation.

Administration to the subject can be by any one or combination of a variety of methods (e.g., parenterally, enterally and/or topically). The appropriate method(s) will depend upon the circumstances of the individual (e.g. the location of the target neuron(s), the condition of the individual, the desired duration of the contact, whether local or systemic treatment is desired). The administration can be by any methods described herein that will result in contact of sufficient an agent that increases IGFBPL-1 activity or levels to the target neuron to induce neuronal outgrowth. For instance, parenteral, enteral and topical administration can be used. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Enteral administration involves the esophagus, stomach, and small and large intestines (i.e., the gastrointestinal tract).

The phrases "systemic administration," "administered systemically", "peripheral administration" and "administered peripherally" as used herein mean the administration of a compound other than directly into the central nervous system, such that it enters the animal's system and, thus, is subject to metabolism and other like processes, for example, subcutaneous administration. Administration may be topical (including ophthalmic, vaginal, rectal, intranasal, epidermal, and transdermal), oral or pulmonary administration, e.g., by inhalation or insufflation, or intracranial, e.g., intrathecal or intraventricular, administration, topically to the eye, or by intraocular injection.

Specific routes of administration and the dosage regimen will be determined by skilled clinicians, based on factors such as the exact nature of the condition being treated, the severity of the condition, and the age and general physical condition of the patient. The invention also provides methods for stimulating the outgrowth of central nervous system neurons following an injury. The method involves administering to a subject an agent that increases IGFBPL-1 activity or levels or analog thereof.

Contacting is optionally achieved by administering the agent that increases IGFBPL-1 activity or levels to a subject by means to thereby contact the desired neuron(s). When administered following an injury, administration of an agent that increases IGFBPL-1 activity or levels alone or in combinations described herein is to be made under conditions effective to stimulate nerve regeneration at the site of the injury and/or under conditions effective to at least partially restore nerve function through the injured nerve(s) (e.g., an injured spinal cord). Restoration of nerve function can be evidenced by restoration of nerve impulse conduction, a detectable increase in conduction action potentials, observation of anatomical continuity, restoration of more than one spinal root level, an increase in behavior or sensitivity, or a combination thereof. Under such circumstances, administration results in contacting the administered factors with the site of injury to thereby promote nerve regeneration (complete or partial).

The term "administering" to a subject includes dispensing, delivering or applying an active compound in a pharmaceutical formulation to a subject by any suitable route for delivery of the active compound to the desired location in the subject, (e.g., the injury, the injured neuron, or the site of desired outgrowth of the neuron). This includes, without limitation, delivery by either the parenteral or oral route, intramuscular injection, subcutaneous/intradermal injection, intravenous injection, buccal administration, transdermal delivery and administration by the rectal, colonic, vaginal, intranasal or respiratory tract route, intraocular, ocular. Another form of administration suitable for treatment of spinal cord injury is injection into the spinal column or spinal canal.

The agent that increases IGFBPL-1 activity or levels or analog thereof is optionally contacted in vivo by introduction into the central nervous system of a subject, e.g., into the cerebrospinal fluid of the subject. In certain aspects of the invention, the agent that increases IGFBPL-1 activity or levels or analog thereof is introduced intrathecally, e.g., into a cerebral ventricle, the lumbar area, or the cisterna magna. In another aspect, an agent that increases IGFBPL-1 activity or levels or analog thereof is introduced intraocularly, to thereby contact retinal ganglion cells or the optic nerve. Modes of administration are described in U.S. Pat. No. 7,238,529.

In some circumstances, the methods described herein will not encompass direct administration into the brain of the subject (e.g., intrastriatal injection). In some circumstances, the methods described herein do not encompass intrathecal administration. That is to say, contacting of the neuron (e.g. the target neuron) is not accomplished by intrathecal administration and/or by direct administration into the brain of the subject (e.g., intrastriatal injection).

In one embodiment, administration occurs following neuronal injury in the subject, not prior to or at the time of neuronal injury.

The agent that increases IGFBPL-1 activity or levels formulation is optionally administered into a subject intrathecally. As used herein, the term "intrathecal administration" is intended to include delivering an agent that increases IGFBPL-1 activity or levels formulation directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of an agent that increases IGFBPL-1 activity or levels to any of the above mentioned sites can be achieved by direct injection of the agent that increases IGFBPL-1 activity or levels formulation or by the use of infusion pumps.

For injection, an agent that increases IGFBPL-1 activity or levels formulation of the invention can be formulated in liquid solutions, preferably in physiologically compatible buffers such as Hank's solution or Ringer's solution. In addition, an agent that increases IGFBPL-1 activity or levels formulation may be formulated in solid form and re-dissolved or suspended immediately prior to use. Lyophilized forms are also included. The injection can be, for example, in the form of a bolus injection or continuous infusion (e.g., using infusion pumps) of an agent that increases IGFBPL-1 activity or levels formulation.

An agent that increases IGFBPL-1 activity or levels formulation is optionally administered by lateral cerebro ventricular injection into the brain of a subject in the inclusive period from the time of the injury to 100 hours thereafter. The injection can be made, for example, through a burr hole made in the subject's skull. In some cases, the encapsulated therapeutic agent is administered through a surgically inserted shunt into the cerebral ventricle of a subject in the inclusive period from the time of the injury to 100 hours thereafter. For example, the injection can be made into the lateral ventricles, which are larger, even though injection into the third and fourth smaller ventricles can also be made. In other cases, the agent that increases IGFBPL-1 activity or levels formulation is administered by injection into the cisterna magna, or lumbar area of a subject in the inclusive period from the time of the injury to 100 hours thereafter.

Duration and Levels of Administration

Contacting of the injured neuron(s) can be anytime following the injury. Preferably, the injured neuron is contacted within 96 hours of formation of the lesion on the neuron to be contacted, and more preferably within 72, 48, 24, or 12 hours.

The treatment of a subject may likewise begin anytime following the injury. Preferably, the treatment progresses upon detection or suspicion of the injury. For example, the treatment can be 6 hr, 12, hr, 18 hr, or 24 hours post injury. Benefit is also expected to be had from treatment that takes place considerably longer after the injury. The injury may have occurred more than three months prior to the treatment, more than one month prior, more than three weeks prior to the treatment, or more than two weeks prior to the treatment, more than one week prior to the treatment or from between 1-6 days prior to the treatment.

In one aspect, the agent that increases IGFBPL-1 activity or levels (e.g., in the form of a pharmaceutical composition) described herein is contacted to a neuron, and/or administered to the subject in the period from the time of injury to 100 hours, for example within 24, 12 or 6 hours after the injury has occurred.

The pharmaceutical composition, used in the method of the invention, contains a therapeutically effective amount of the agent that increases IGFBPL-1 activity or levels. A "therapeutically effective amount" refers to an amount effective, at dosages and for periods of time necessary, to achieve the desired result (e.g., a neurosalutary effect, detectable neuronal outgrowth). A therapeutically effective amount of an agent that increases IGFBPL-1 activity or levels may vary according to factors such as the disease state, age, and weight of the subject, and the ability of an agent that increases IGFBPL-1 activity or levels or analogue thereof (alone or in combination with one or more other agents) to elicit a desired response in the subject. Dosage regimens may be adjusted to provide the optimum therapeutic response. A therapeutically effective amount is also one in which any toxic or detrimental effects of an agent that increases IGFBPL-1 activity or levels or analogue thereof are outweighed by the therapeutically beneficial effects. The term "therapeutically effective amount" refers to an amount that is sufficient to effect a therapeutically reduction in a symptom associated with neuronal injury, disease, disorder or condition described herein, when administered to a typical subject who has said injury, disease, disorder, condition. A therapeutically significant reduction in a symptom is, e.g. about 10%, about 20%, about 30%, about 40%, about 50%, about 60%, about 70%, about 80%, about 90%, about 100%, about 125%, about 150% or more as compared to a control or non-treated subject. In some embodiments the term "therapeutically effective amount" refers to the amount that is safe and sufficient to prevent or delay the development and further spread of neuronal injury, disease, or other disease symptoms. The amount can also cure or cause the disease, disorder or condition to go into remission, slow the course of, or otherwise inhibit progression.

Any of the subject formulations are administered in a single dose or in divided doses. Dosages for the formulations of the present invention may be readily determined by techniques known to those of skill in the art or as taught herein. For example, the composition is present in a concentration range of 0.1-25%, 0.1% to 20%, or 0.1% to 10%, with preferred ranges between 1-5% or 2-2.5% (mg/ml). Exemplary liquid formulations for eye drops contain 2-2.5% (mg/ml) of the composition. Preferred formulations are in the form of a solid, a paste, an ointment, a gel, a liquid, an aerosol, a mist, a polymer, a film, an emulsion, or a suspension. The formulations are administered topically, e.g., the composition is delivered to an ocular or adnexal tissue to directly contact that tissue. For example, the composition is incorporated into or coated onto a contact lens, which is applied directly to the ocular or adnexal tissue.

For example, a non-limiting range for a therapeutically effective concentration of an agent that increases IGFBPL-1 activity or levels is 5 µM to 1 mM. A non-limiting range for a therapeutically effective concentration of an agent that increases IGFBPL-1 activity or levels is at least 25 µM to 1 mM. In a particularly preferred embodiment, the therapeutically effective concentration of an agent that increases IGFBPL-1 activity or levels is 10-25 µM, or 25-50 µM. In a particularly preferred embodiment, the therapeutically effective concentration of an agent that increases IGFBPL-1 activity or levels is 25-50 µM, 50-100 µM, or 100-150 µM. Dosage values may vary with the severity of the condition to be alleviated. For any particular subject, specific dosage regimens may be adjusted over time according to the individual need and the professional judgment of the person administering or supervising the administration of an agent that increases IGFBPL-1 activity or levels or analogue thereof and that dosage ranges set forth herein are exemplary only and are not intended to limit the scope or practice of the claimed invention.

A therapeutically effective amount or dosage of an agent that increases IGFBPL-1 activity or levels ranges from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. A non-limiting range for a therapeutically effective in vivo concentration in tissue containing the injury is 5 µM to 5 mM.

In one embodiment, administration occurs following neuronal injury in the subject, not prior to or at the time of neuronal injury.

In Vitro Treatment of Neurons

Neurons can further be contacted with a therapeutically effective amount of an agent that increases IGFBPL-1 activity or levels, in vitro or ex vivo. Accordingly, neuron cells can be isolated from a subject and grown in vitro, using techniques well known in the art. Briefly, a neuron cell culture can be obtained by allowing neuron cells to migrate out of fragments of neural tissue adhering to a suitable substrate (e.g., a culture dish) or by disaggregating the tissue, e.g., mechanically or enzymatically, to produce a suspension of neuron cells. For example, the enzymes trypsin, collagenase, elastase, hyaluronidase, DNase, pronase, dispase, or various combinations thereof can be used. Trypsin and pronase give the most complete disaggregation but may damage the cells. Collagenase and dispase give a less complete dissagregation but are less harmful. Methods for isolating tissue (e.g., neural tissue) and the disaggregation of tissue to obtain cells (e.g., CNS neuron cells) are described in Freshney R. L, Culture of Animal Cells, A Manual of Basic Technique, Third Edition, 1994, the contents of which are incorporated herein by reference.

Such cells can be subsequently contacted with an agent that increases IGFBPL-1 activity or levels at levels and for a duration of time as described above. Once modulation of neuronal outgrowth has been achieved in the neuron cells, these cells can be re-administered to the subject, e.g., by implantation.

Eluting Devices

The invention also provides an agent that increases IGFBPL-1 activity or levels-eluting or an agent that increases IGFBPL-1 activity or levels-impregnated implantable solid or semi-solid devices, for implantation into the CNS or the PNS. Examples of CNS implantable devices include polymeric microspheres (e.g. see Benny et al., Clin Cancer Res. (2005) 11:768-76) or wafers (e.g. see Tan et al., J Pharm Sci. (2003) 4:773-89), biosynthetic implants used in tissue regeneration after spinal cord injury (reviewed by Novikova et al., Curr Opin Neurol. (2003) 6:711-5), biodegradable matrices (see e.g. Dumens et al., Neuroscience (2004) 125:591-604), biodegradable fibers (see e.g. U.S. Pat. No. 6,596,296), osmotic pumps, stents, adsorbable gelatins (see e.g. Doudet et al., Exp Neurol. (2004) 189:361-8). Preferred devices are particularly tailored, adapted, designed or designated for CNS implantation. The implantable device may contain one or more additional agents used to promote or facilitate neural regeneration, as described herein.

The invention is further illustrated in the following non-limiting examples illustrated in the accompanying Figures.

Example 1: Promotion of Optic Nerve Regeneration by IGFBPL-1

The experiments described herein were aimed to elucidate the functional role and mechanisms of IGFBPL-1 on RGC survival and axon extension in mice. The expression pattern of IGFBPL-1 in the developing retina was examined in retinas at different developmental stage, ranging from embryonic day 16 through adult, using immunohistochemistry, western blot and quantitative RT-PCR. Retinal ganglion cells were purified using magnetic beads conjugated with Thy1.2 antibody from new born mouse pups at postnatal day 0 (P0), and cultured for up to five days in the presence or absence of IGFBPL-1 and/or IGF-I proteins. RGC survival and axonal growth were evaluated after three days in culture following LIVE/DEAD® and ß-III-tubulin immunostaining. Lentiviral shRNAs were used to knockdown the expression of IGFBPL-1 and/or IGF-I in culture. The functional role of IGFBPL-1 in RGC development was further evaluated in IGFBPL-1 knockout (KO) mouse. RGC morphology and number were recorded using retinal vertical sections or whole-mount preparation. The number of axons in the optic nerve head was counted under electron microscopy. Data collected from the IGFBPL-1 KO mice were compared with that obtained from age-matched wildtype C57BL/6 littermates.

As shown in FIGS. 1-9, expression of IGFBPL-1 was restricted to the RGC layer in the retina with a transient high expression at E16-E18 and largely down-regulated postnatally. Moreover, the addition of IGFBPL-1 alone or together with IGF-I in P0 RGC cultures significantly promoted axonal extension. Mice deficient for IGFBPL-1 exhibit a largely reduced number of axons in the optic nerve without significantly altering the morphology and number of RGCs.

Specifically, FIG. 1 shows immuno-detection of IGFBPl-1 expression in the developing mouse retina. Transverse retinal sections taken from mice at embryonic day 16 (E16), E18 and postnatal day 0 (P0) and P10 were immunolabeled for IGFBPL-1 (red) and were counter-stained with a nuclear marker DAPI (blue). Expression of IGFBPL-1 was detected in the ganglion cell layer (GCL) of mice, with highest expression E16 to E18. The level of IGFBPL-1 expression decreased drastically after postnatal day 0 (P0) and was absent in mature retinal ganglion cells. As shown in FIG. 1, this pattern of IGFBPL-1 expression inversely correlates with the loss of optic nerve regenerative capacity by retinal ganglion cells.

Figure 2A:
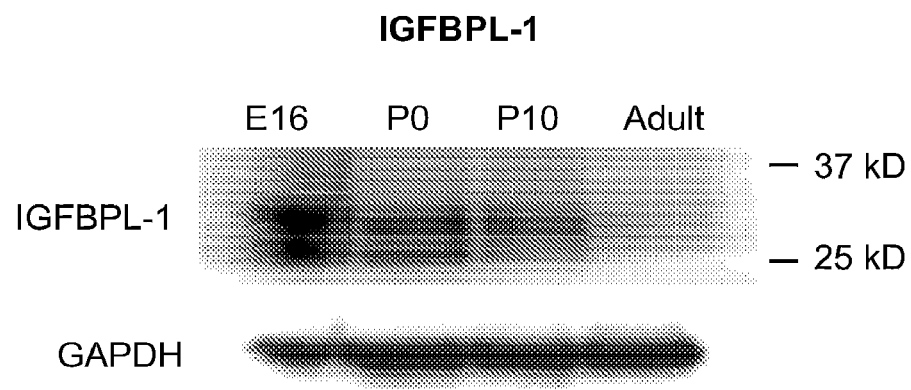
FIG. 2A-FIG. 2B are an immunoblot and a bar chart, respectively.
Figure 2B:
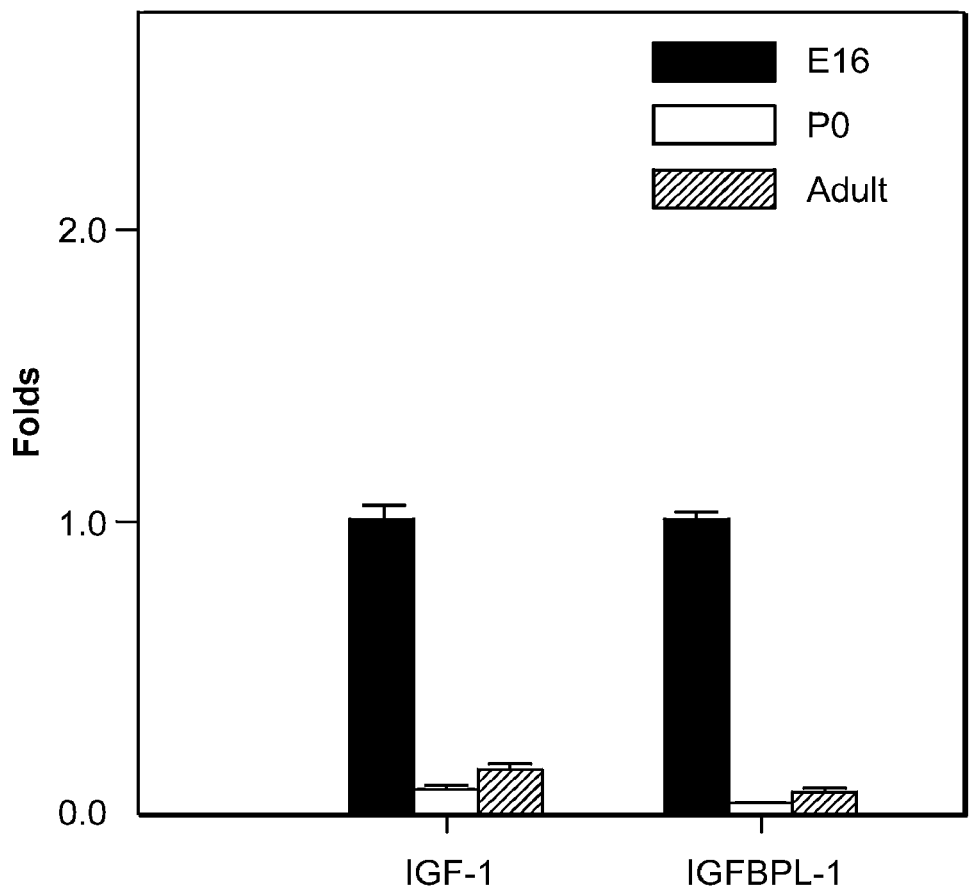

Western blot analysis of IGFBPL-1 expression is illustrated in FIG. 2A. FIG. 2B is a qRG-PCR analysis of IGFBPL-1 and IGF-1 mRNA. The IGFBPL-1 protein (FIG. 2A) and mRNA (FIG. 2B) levels were measured using Western blot and quantitative RT-PCR, respectively. IGFBPL-1 protein and mRNAs are highly expressed in E16 retinas, but are decreased in P0 and older retina.

As shown in FIG. 3, IGFBPL-1 promotes RGC neurite outgrowth. RGC neurite outgrowth in the absence (FIG. 3A) and presence (FIG. 3B) of IGFBPL-1 promotes in RGC cell culture. Retinal ganglion cells (RGCs) isolated from P0 mice were cultured in the absence (control) and presence of IGFBPL-1 (IGFBPL-1) for 3 days and were immunolabeled with primary antibody against a RGC specific marker Tuj1 (red). Note that RGCs extend long neurite in IGFBPL-1-treated cultures as compared to control culture group.

Quantification of RGC neurite outgrowth in culture in the presence of increasing amounts of IGFBPL-1 is shown in FIG. 4. * $P<0.01$ compared to the control. IGFBPL-1 stimulates neurite outgrowth in RGC cultures isolated from P0 mouse pups.

FIGS. 5 (I) A and B and FIGS. 5 (II) A and B are western blots showing binding of IGFBP-1 with IGF-I using mouse recombinant IGFBPL-1 and IGF-1 (FIG. 5 (I)) and retina lysates (FIG. 5 (II)). The co-immunoprecipitation of IGFBPL-1 and IGF-1 demonstrates that IGFBPL-1 directly interacts with IGF-1.

Figure 6A:
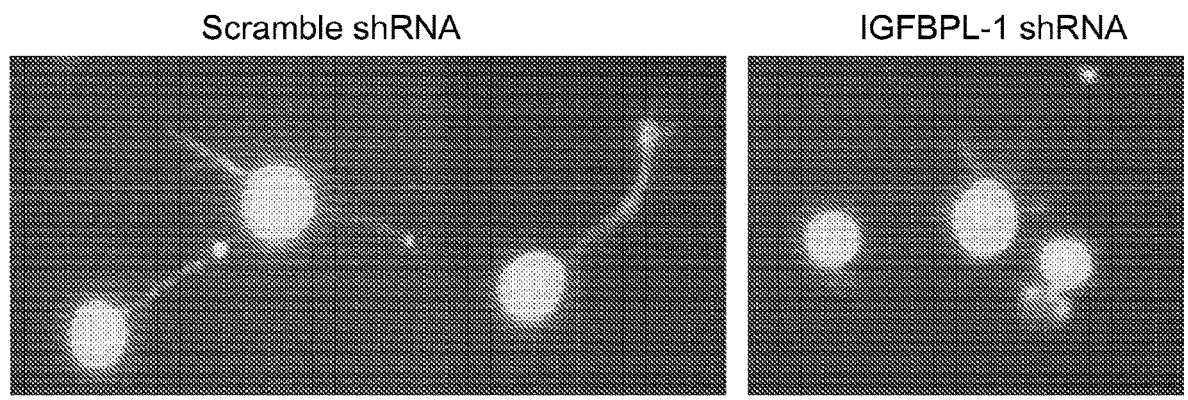
FIG. 6A-FIG. 6B are a photomicrograph and a bar chart, respectively, demonstrating that knockdown of IGFBPL-1 by lentiviral shRNA impairs neurite outgrowth in cultured P0 RGCs.
Figure 6B:
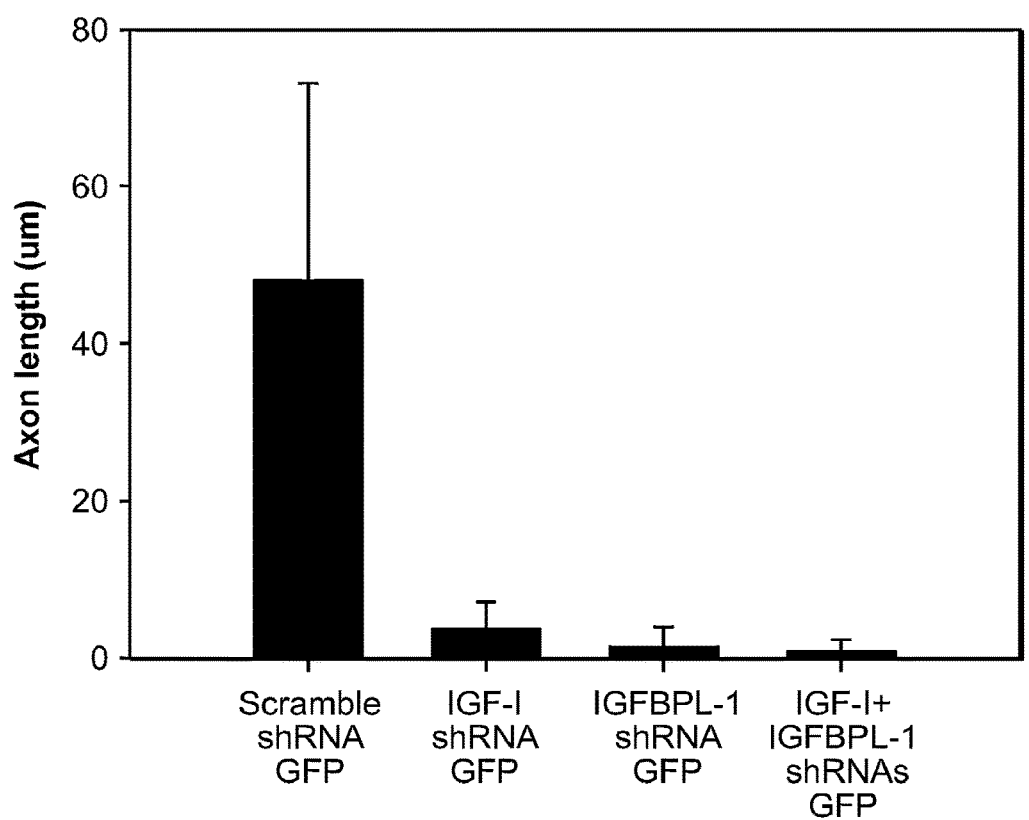

As shown in FIG. 6, knockdown of IGFBPL-1 by lentiviral shRNA impairs neurite outgrowth in cultured P0 RGCs. Immunofluorescence images (FIG. 6A) and a bar chart (FIG. 6B) show the impairment of neurite outgrowth in cultured P0 RGC following knockdown of IGFBPL-1 by scramble shRNA and lentiviral shRNA.

Immunofluorescence images showing that blockade of IGFI-1 signaling abolishes IGFBPL-1 induced axon growth in P0 RGC cultures are shown in FIG. 7. Specifically, the figure shows images of RGC axon morphology. P0 RGC cultures treated with IGFBPL-1, IGF-1 or both exhibited robust neurite outgrowth. Application of NBI-31772, a pan inhibitor that generally disrupts the binding of IGF-1 with its binding proteins, H1356 (inhibitor of IGF-1 binding with its receptor), or an IGF-1 neutralizing antibody abolishes the neurite growth effect of IGFBPL-1. The results show that IGFBPL-1 acts through IGF-1-mediated pathways to stimulate RGC neurite outgrowth.

Figure 8:
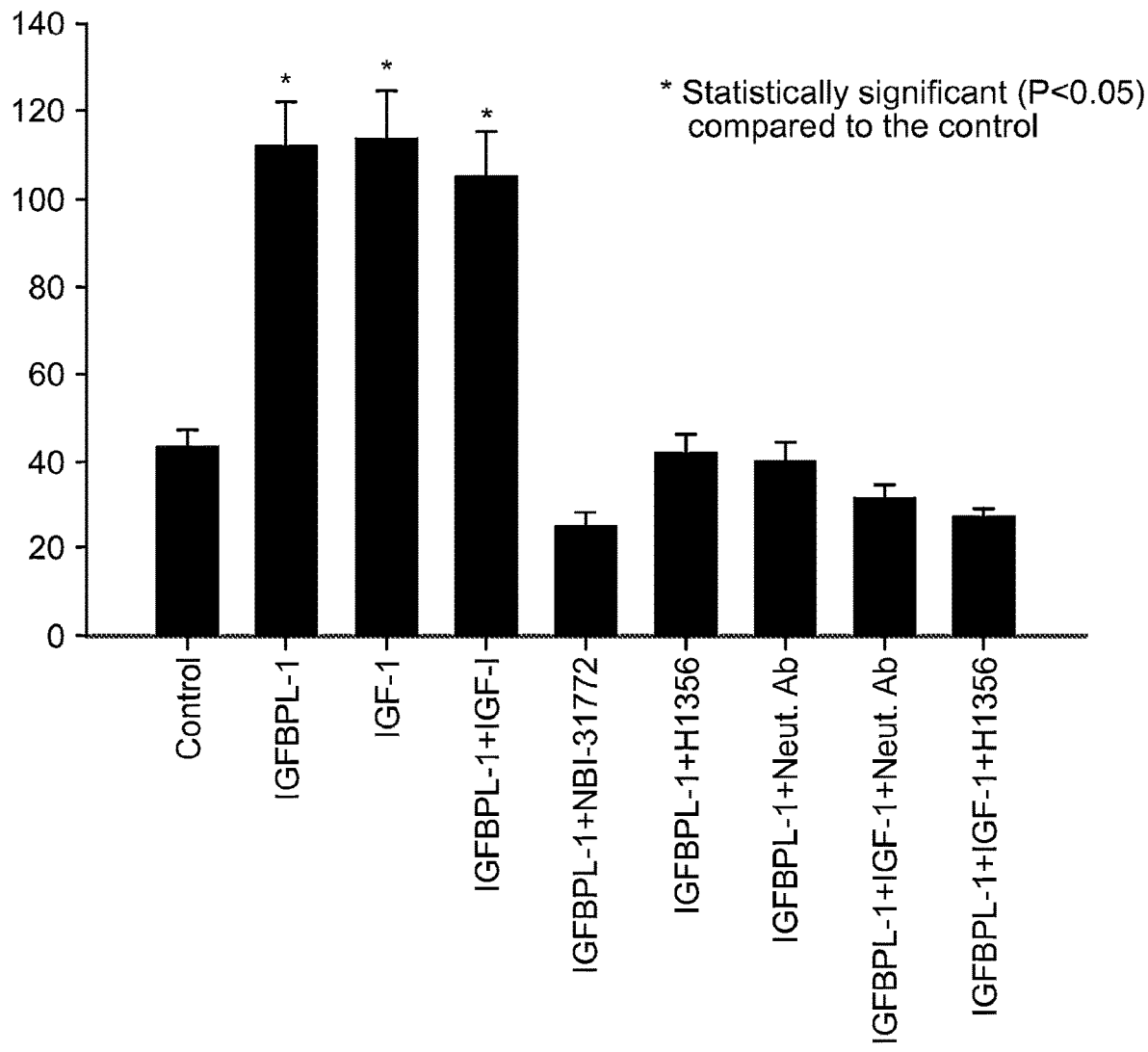
FIG. 8 is a histogram showing quantification of axon growth from cultured P0 RGCs in the presence of control; IGFPL-1; IGF-1; IGFPL-1+IGF-1; IGFBPL-1+NBI-31772; IGFBPL-1+H1356; IGFBPL-1+Neut. Ab; IGFBPL-1+IGF-I+Neut. Ab; and IGFBPL-1+IGF-I+H1356.

Quantification of axon growth from cultured P0 RGCs in the presence of control; IGFPL-1; IGF-1; IGFPL-1+IGF-1; IGFBPL-1+NBI-31772; IGFBPL-1+H1356; IGFBPL-1+Neut. Ab; IGFBPL-1+IGF-I+Neut. Ab; and IGFBPL-1+IGF-I+H1356 is shown in FIG. 8.

Figure 9A:
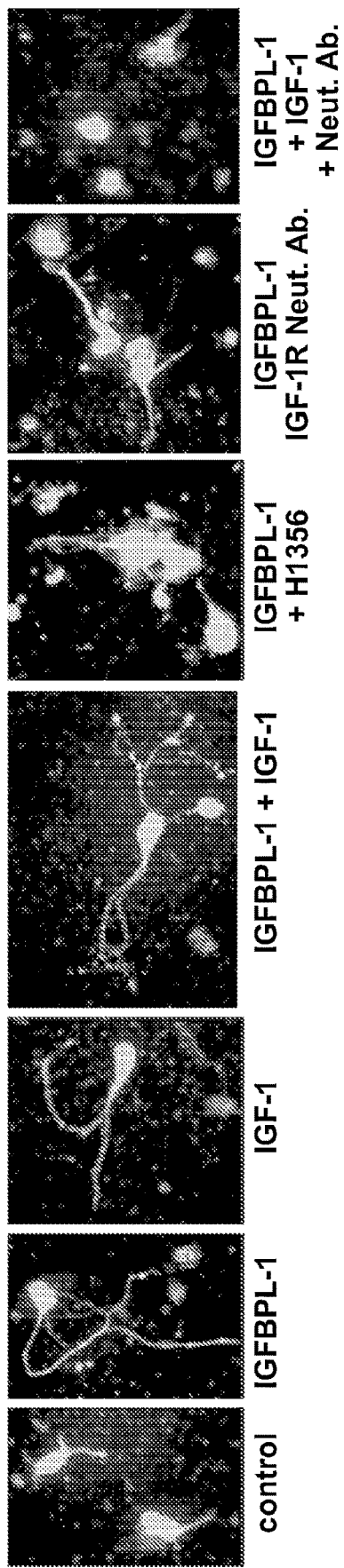
FIG. 9A-FIG. 9B are a series of photomicrographs and a bar chart showing that blockade of IGF-1 pathway abolishes IGFBPL-1 induced neurite growth in hippocampal neuronal cultures.
Figure 9B:
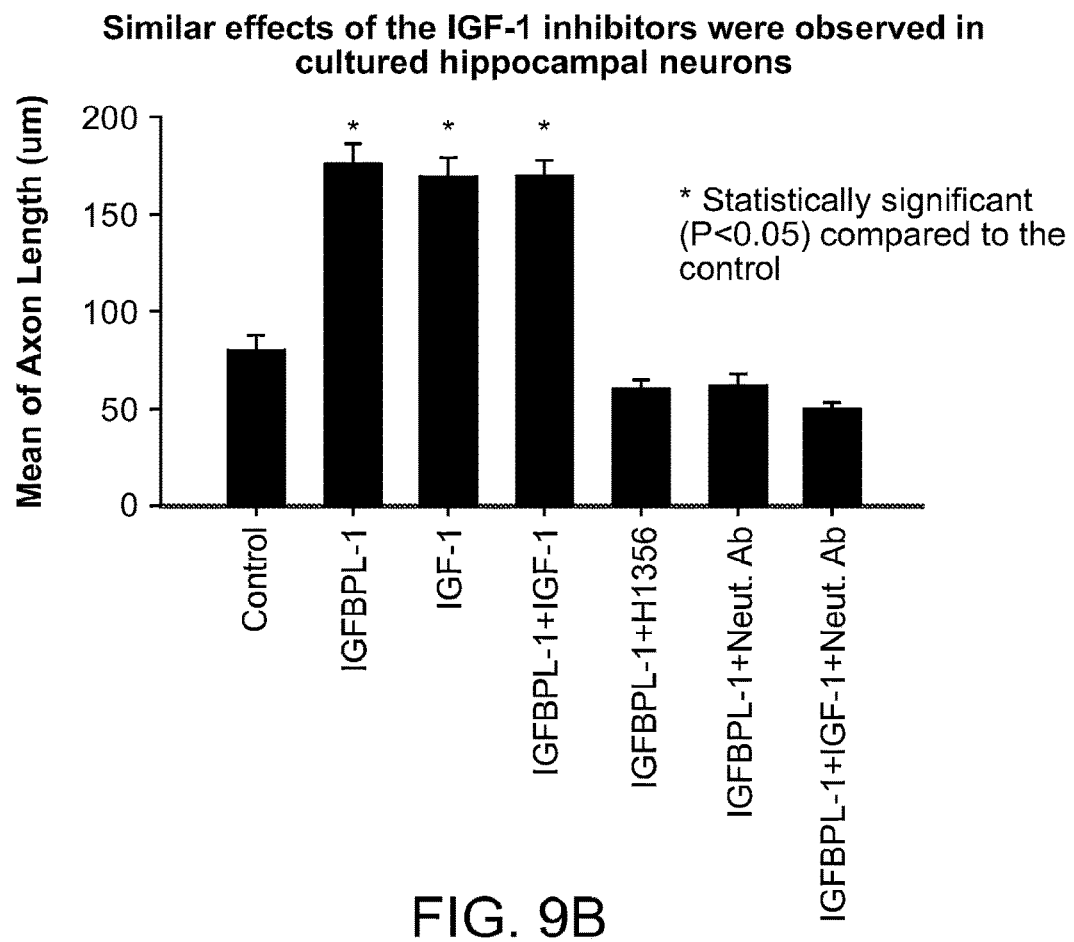

As shown in FIG. 9, blockade of IGF-1 pathway abolishes IGFBPL-1 induced neurite growth in hippocampal neuronal cultures. FIG. 9A shows hippocampal neurons stained with beta III tubulan. FIG. 9B are histograms showing quantification of neurite outgrowth in control; and neurons exposed to IGFBPL-1; IGF-1; IGFBPL-1+IGF-1; IGFBPL-1+H1356; IGFBPL-1+Neut. Ab; IGFBPL-1+IGFI-1+Neut. Ab. Similar effects of the IGF-1 inhibitors were observed in cultured hippocampal neurons.

Figure 10:
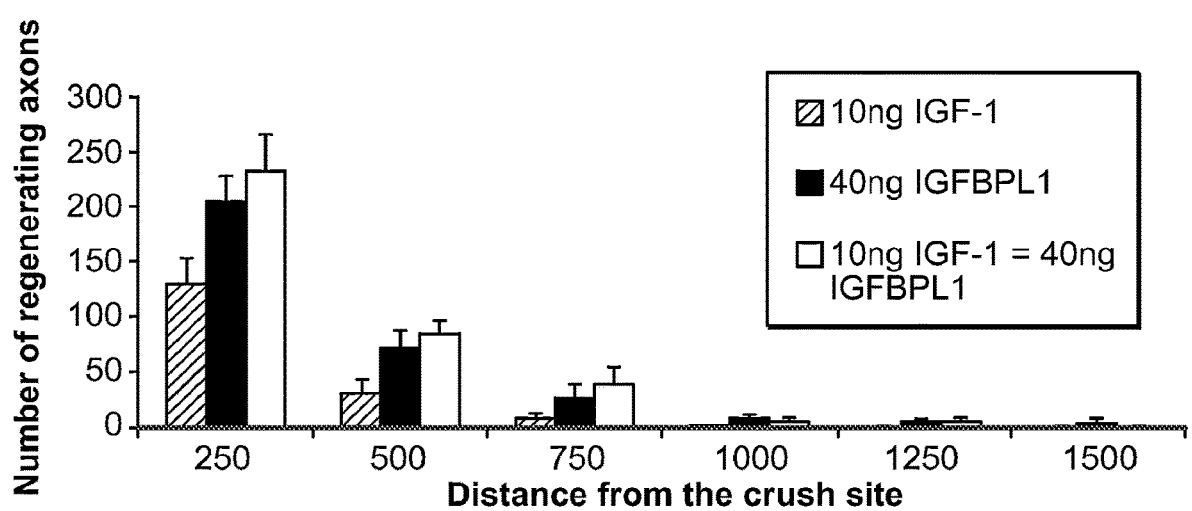
FIG. 10 is a bar chart showing that IGF-I and IGFBPL1 enhance optic nerve regeneration in vivo. Intravitreous delivery of IGFBPL1, either in the presence or absence of IGF-I, significantly promotes the regeneration of RGC axons after optic nerve crush in mice. IGF-1 (n=60). IGFBPL-1 (n=7). IGF1+IGFBPL1 (n=6).
Figure 11A:
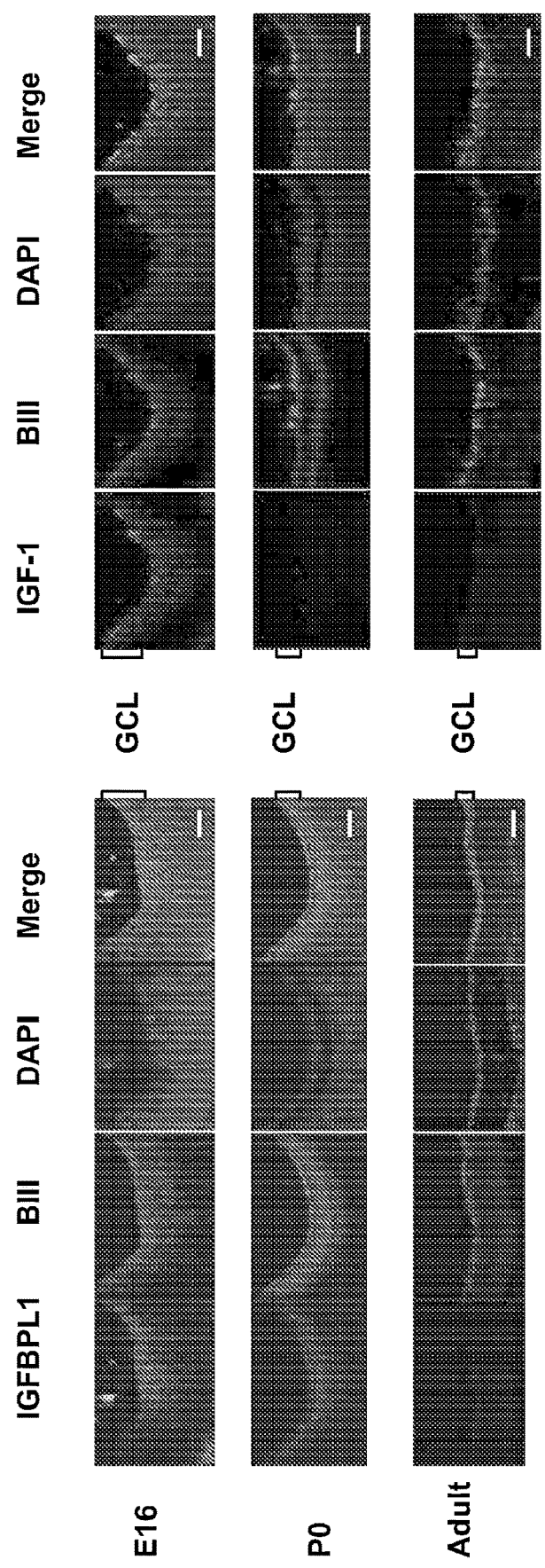
FIG. 11A-FIG. 11E are a series of photomicrographs, a series of immunoblots, and a bar chart illustrating the expression of IGFBPL1 and IGF-I in the developing mouse retina. The figure shows epifluorescence photomicrographs of immunostaining of the developing mouse retina taken at embryonic day 16 (E16), postnatal day 0 (P0) and adult, using primary antibodies (green) against IGFBPL1 (left panel) and IGF-I (right panel). DAPI (blue) was used to reveal retinal laminar structure and anti-beta-III tubulin (BIII; red) was used to label retinal ganglion cells (RGCs). Note that both IGFBPL1 and IGF-I were highly expressed in RGCs at E16, when RGCs are capable of grow and regenerate the optic nerve, but their expression was down regulated after birth, correlating with the developmental onset of optic nerve regenerative failure. GCL, ganglion cell layer. Scale bars for FIG. 11A: 50 µm.
Figure 11B:
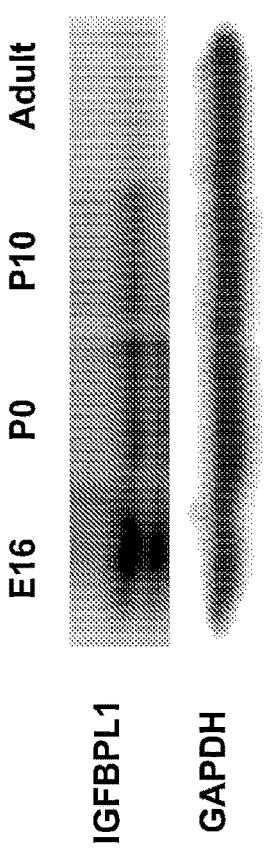
Figure 11C:
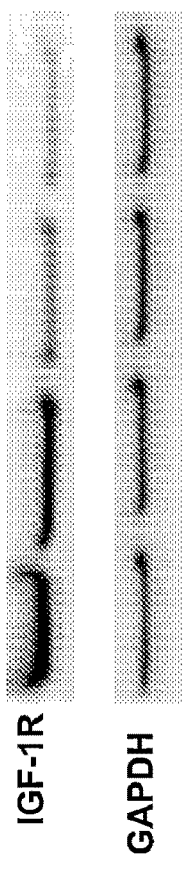
Figure 11D:
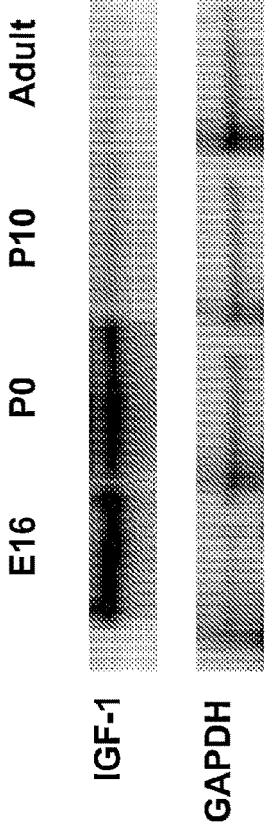
Figure 11E:
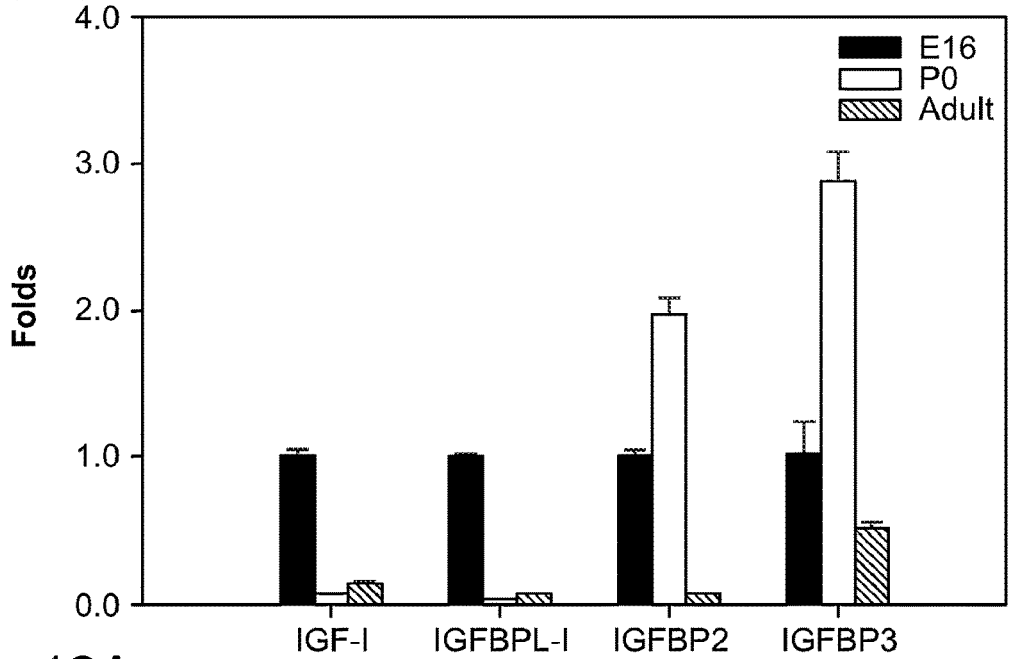

As shown in FIG. 10, IGF-I and IGFBPL1 enhance optic nerve regeneration in vivo. Intravitreous delivery of IGFBPL1, either in the presence or absence of IGF-I, significantly promotes the regeneration of RGC axons after optic nerve crush in mice. IGF-1 (n=60). IGFBPL-1 (n=7). IGF1+IGFBPL1 (n=6).

The expression of IGFBPL1 and IGF-I in the developing mouse retina is shown in FIG. 11. The figure shows epifluorescence photomicrographs of immunostaining of the developing mouse retina taken at embryonic day 16 (E16), postnatal day 0 (P0) and adult, using primary antibodies (green) against IGFBPL1 (left panel) and IGF-I (right panel). DAPI (blue) was used to reveal retinal laminar structure and anti-beta-III tubulin (BIII; red) was used to label retinal ganglion cells (RGCs). Both IGFBPL1 and IGF-I were highly expressed in RGCs at E16, when RGCs are capable of grow and regenerate the optic nerve, but their expression was down regulated after birth, correlating with the developmental onset of optic nerve regenerative failure. GCL, ganglion cell layer. Scale bars for FIG. 11A: 50 µm. FIG. 11B-FIG. 11D are photographs of western blots of IGF-I, IGFBPL1 and IGF-IR in the developing mouse retina. FIG. 11E is a bar chart showing the quantification of IGF-I, IGFBPL1, IGFBP2 and IGFBP3 mRNA expression in the developing mouse retina, using quantitative RT-PCR. The data confirmed high expression of IGF-I, IGFBPL1 and IGFIR in the E16 retina but their expression is downregulated in the postnatal stage.

Figure 12A:
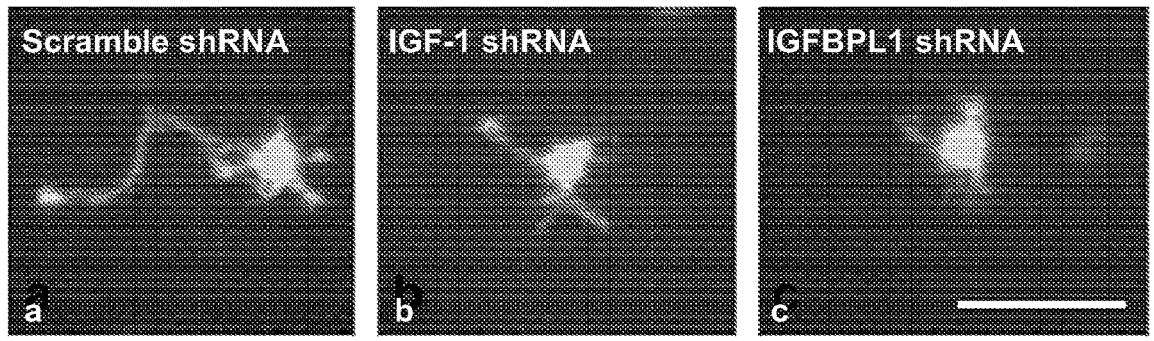
FIG. 12A-FIG. 12B are a series of photomicrographs and a bar chart demonstrating that knockdown of IGF-I or IGFBPL1 impairs RGC neurite outgrowth.
Figure 12B:
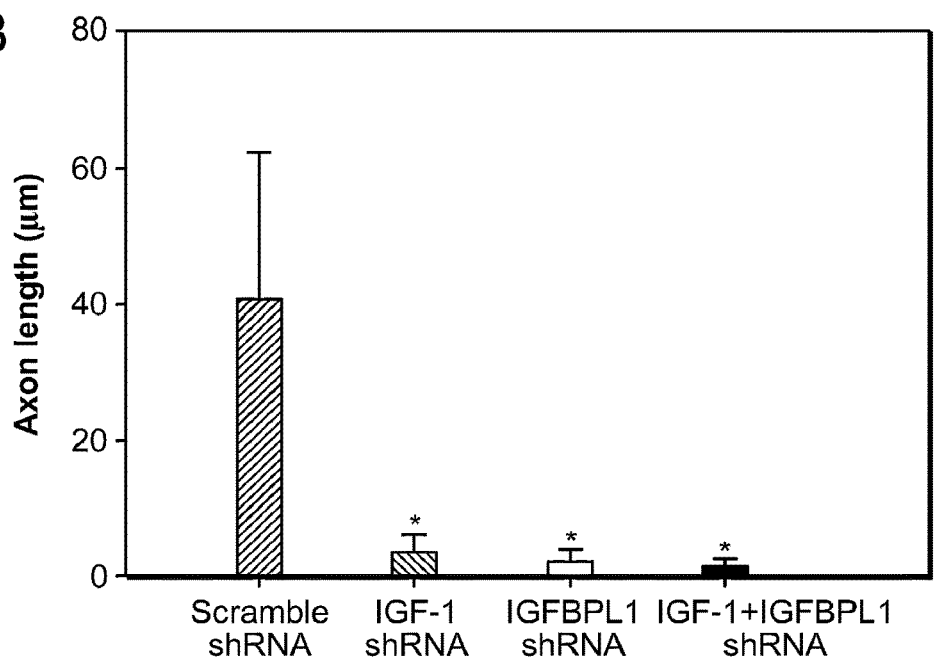

Knockdown of IGF-I or IGFBPL1 impairs RGC neurite outgrowth (FIG. 12). FIG. 12A shows representative photomicrographs of cultured P0 RGCs that were infected by lentiviral vector carrying scramble shRNA (a), IGF-I shRNA (b), and IGFBPL1 shRNA (c). All lentiviral constructs contained an EGFP reporter gene. FIG. 12B shows the quantification of neurite length in P0 RGC cultures that were treated with lentiviral vector carrying different shRNAs. *$P<0.01$ as compared to Scramble shRNA treated group (by two tailed student t-test). Knockdown of ether IGF-I or IGFBPL1 impaired RGC neurite outgrowth in culture, indicating the requirement of both signals for RGC axon extension.

Figure 13A:
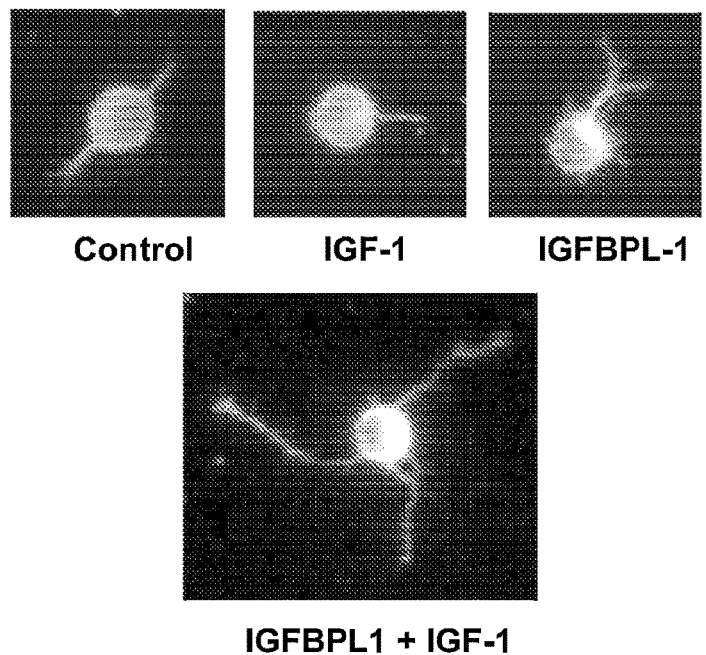
FIG. 13A-FIG. 13C are a series of photomicrographs and bar charts demonstrating that the addition of IGF-I and IGFBPL1 promotes RGC axonal growth.
Figure 13B:
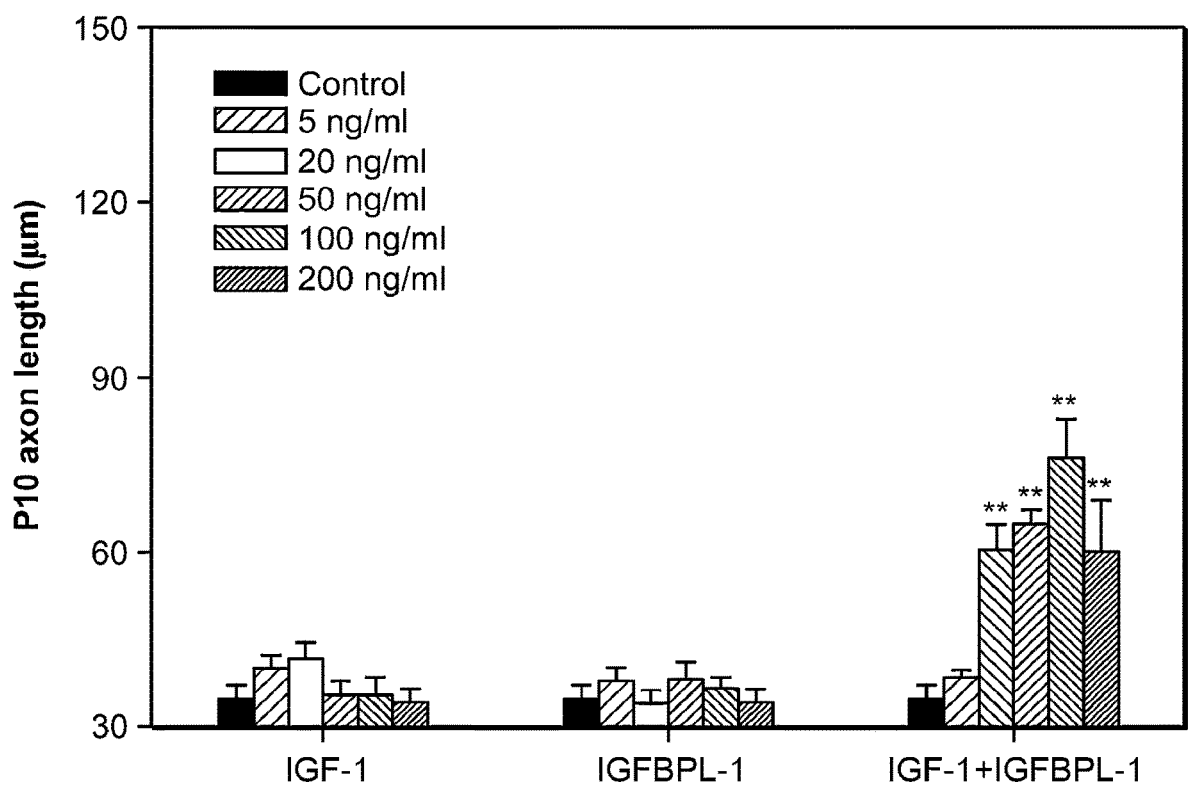
Figure 13C:
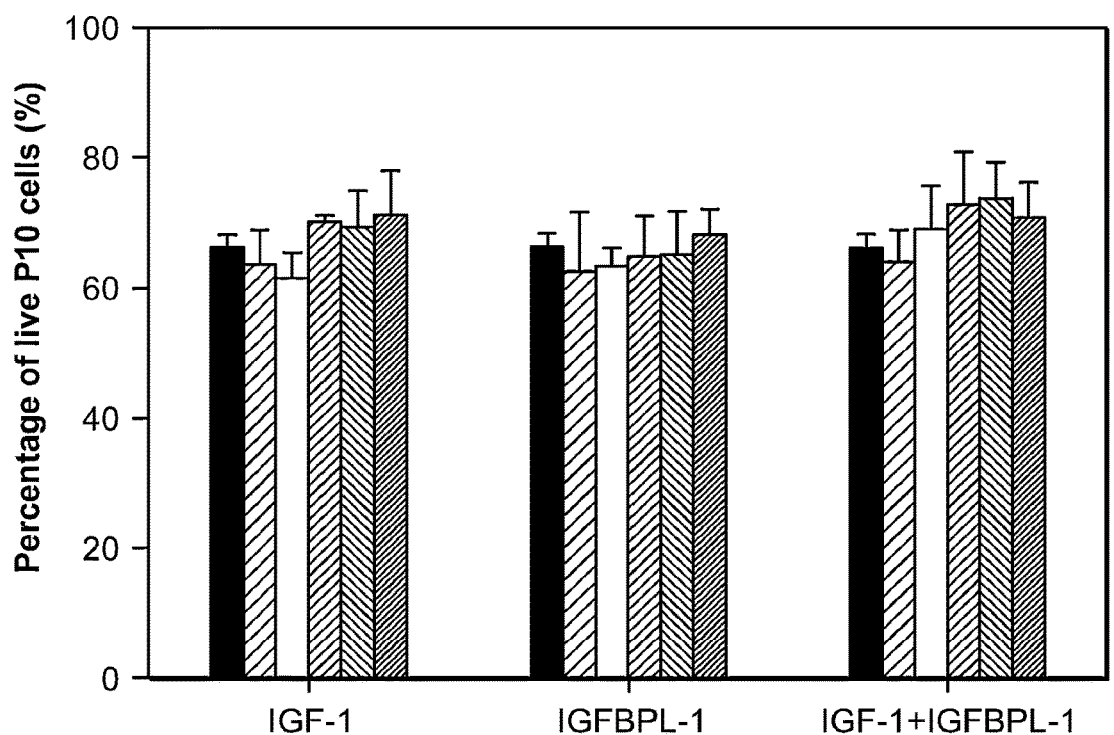

The addition of IGF-I and IGFBPL1 promotes RGC axonal growth. FIG. 13A shows representative photomicrographs of cultured RGCs derived from P10 mice. Cells were treated with control, IGF-I, IGFBPL1 or both for 3 days and were immunostained with BIII-tubulin to reveal axons. FIG. 13B shows the quantification of axon length from cultured RGCs. Addition of IGF-I or IGFBPL1 alone does not promote neurite outgrowth, and both IGF-I and IGFBPL-1 are required to stimulate axon elongation in cultured RGCs derived from P10 mouse pups. FIG. 13C shows the quantification of RGC survival. Either IGF-I or IGFBPL1 affect the survival of RGCs derived from P10 mice. **$P<0.01$ as compared to controls by t-test.

Figure 14A:
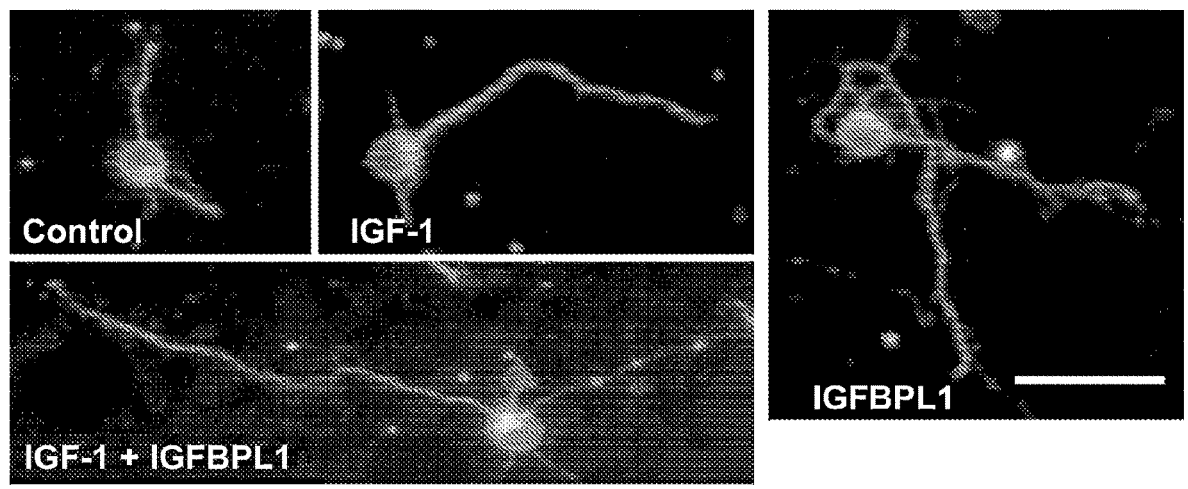
FIG. 14A-FIG. 14C are a series of photomicrographs and bar charts demonstrating that the addition of IGF-I and IGFBPL1 promotes both RGC survival and neurite outgrowth at an early developmental stage.
Figure 14B:
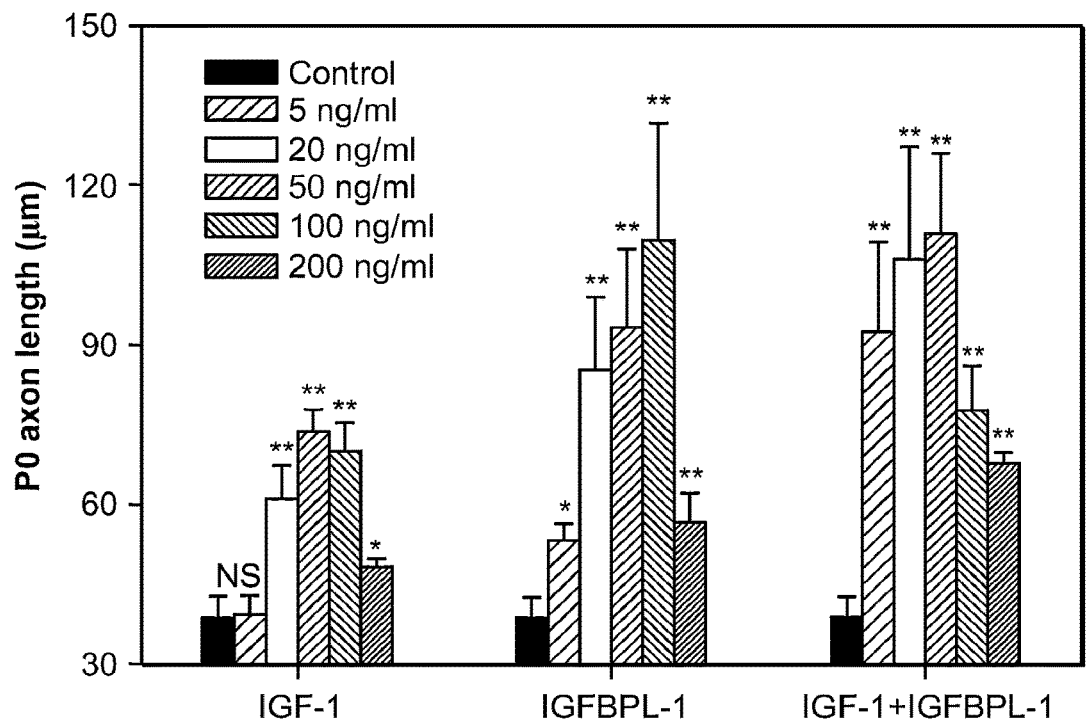
Figure 14C:
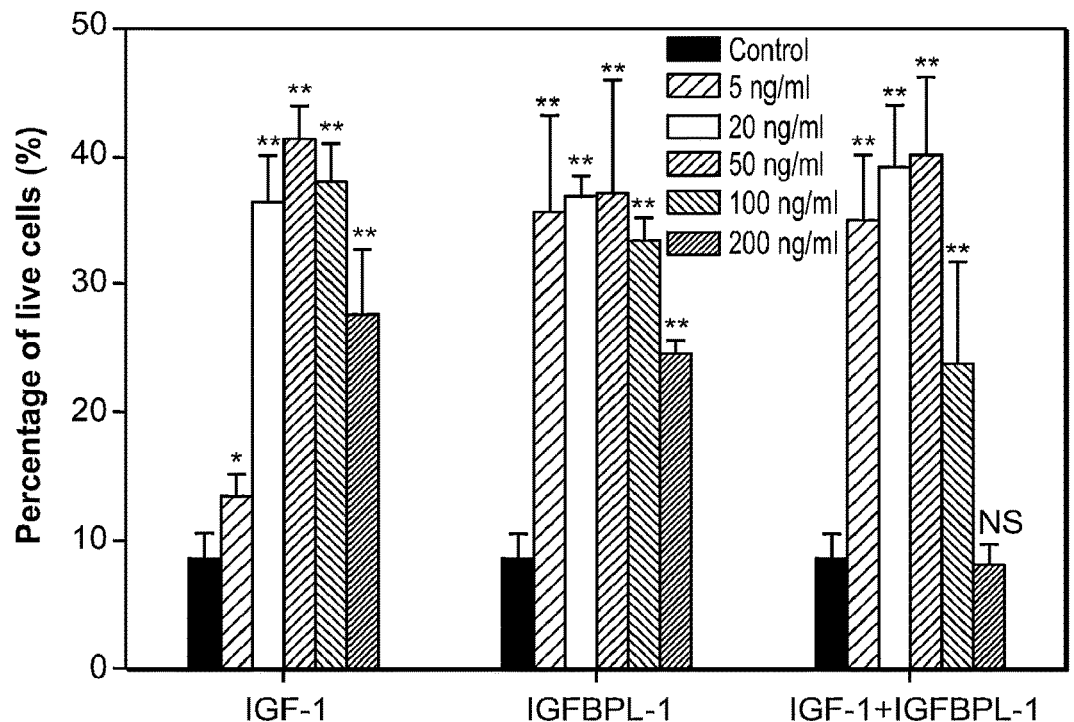

As shown in FIG. 14, the addition of IGF-I and IGFBPL1 promotes both RGC survival and neurite outgrowth at an early developmental stage. FIG. 14A shows representative epifluorescence photomicrographs of cultured P0 RGCs under different treatments. Cells were immunostained with BIII-tubulin. FIG. 14B and FIG. 14C show the quantification of RGC neurite length (FIG. 14B) and cell survival (FIG. 14C). Administration of either IGF-I or IGFBPL1 promotes both neurite outgrowth and cell survival. **$P<0.01$, *$P<0.05$, NS: no significance, as compared to the control group by two tailed student t-test.

Figure 15A:
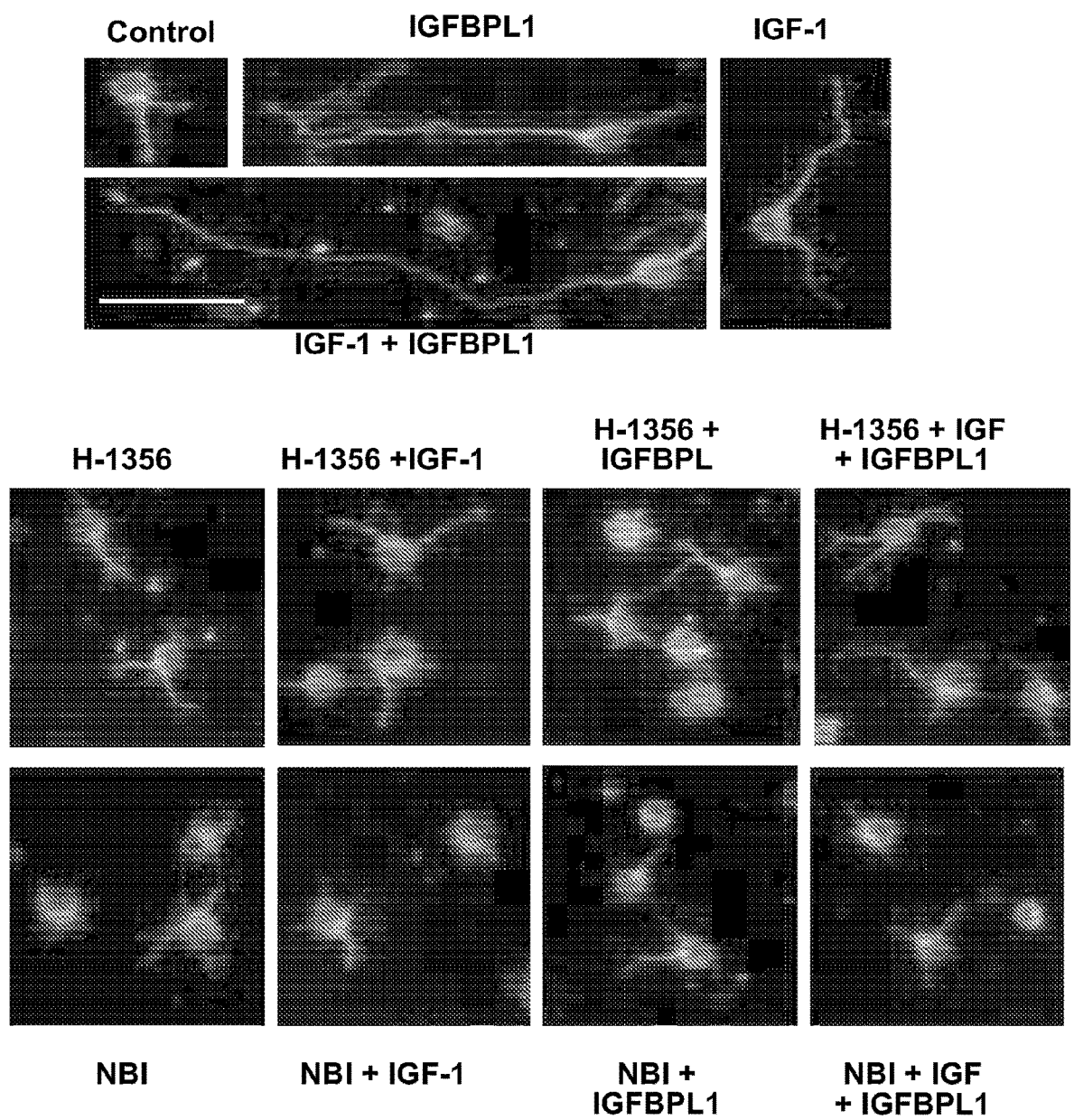
FIG. 15A-FIG. 15B are a series of photomicrographs and a bar chart demonstrating that blockage of IGF-I pathway abolishes IGFBPL1 induced axonal growth.
Figure 15B:
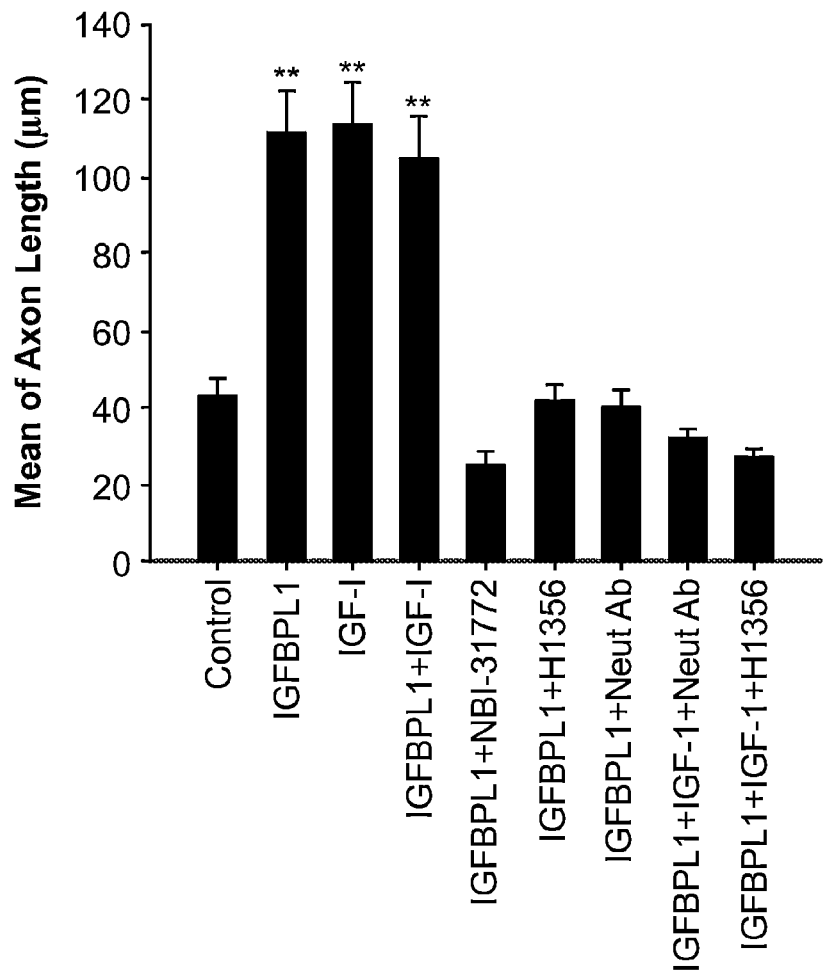

Blockage of IGF-I pathway abolishes IGFBPL1 induced axonal growth (FIG. 15). FIG. 15A shows representative photomicrographs of cultured P0 RGCs that were treated with IGF-I or IGFBPL1 in the presence or absence of various IGF-1 inhibitors or neutralizing antibodies. Cells were immunostained with BIII-tubulin. FIG. 15B shows the quantification of axon length in cultured RGCs. **$P<0.01$ as compared to the control group by t-test. Disruption of IGF-I signaling by administration of IGF-I neutralizing antibody, IGF-IR inhibitor or inhibitor of IGF-I and IGFBP binding abolishes the growth promoting activity of IGFBPL1, suggesting that the activity of IGFBPL1 requires the presence of IGF-I signaling.

Figure 16:
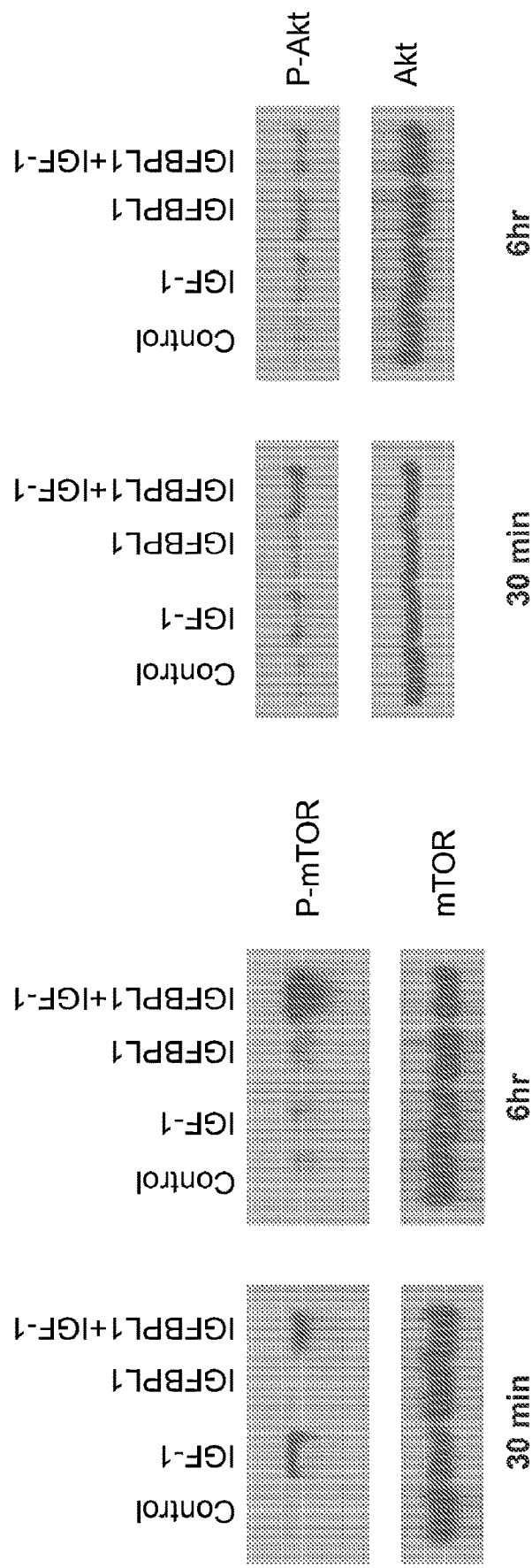
FIG. 16 is a series of immunoblots showing that IGFBPL1 prolongs the phosphorylation of mammalian target of rapamycin (mTOR), a serine/threonine protein kinase that regulates cell growth, cell proliferation, cell motility, cell survival, protein synthesis, and transcription. P10 retinas were dissected and incubated with IGF-I, IGFBPL1 and IGF-I+IGFBPL1 for 30 min or 6 hours at 37° C. Retina lysates were prepared for western blotting, using antibodies against IGF-I-mediated downstream signals, mTOR and Akt. The results showed that IGF-I alone or together with IGFBPL1 can active the mTOR and Akt (increased level of phosphorylated mTOR and Akt), and furthermore, the level of phosphorylated mTOR increased dramatically when the retinas were incubated with IGF-1+IGFBPL1 for 6 hours.

FIG. 16 is a series of immunoblots showing that IGFBPL1 prolongs the phosphorylation of mammalian target of rapamycin (mTOR), a serine/threonine protein kinase that regulates cell growth, cell proliferation, cell motility, cell survival, protein synthesis, and transcription. P10 retinas were dissected and incubated with IGF-I, IGFBPL1 and IGF-I+IGFBPL1 for 30 min or 6 hours at 37° C. Retina lysates were prepared for western blotting, using antibodies against IGF-I-mediated downstream signals, mTOR and Akt. The results showed that IGF-I alone or together with IGFBPL1 can active the mTOR and Akt (increased level of phosphorylated mTOR and Akt), and furthermore, the level of phosphorylated mTOR increased dramatically when the retinas were incubated with IGF-1+IGFBPL1 for 6 hours.

The results presented herein demonstrate that IGFBPL-1 serves as an important regulator of RGC axonal growth during retinal development, likely functioning by facilitating the IGF-I signaling pathway. These studies provide new information regarding regulating RGC axon growth, protection, regeneration and repair.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
Sequence total quantity: 4
SEQ ID NO: 1         moltype = DNA  length = 1093
FEATURE              Location/Qualifiers
source               1..1093
                     mol_type = genomic DNA
                     organism = Homo sapiens
```

```
SEQUENCE: 1
ccgccgctgt cccggagcaa gccatgccgc gcttgtctct gctcttgccg ctgctgcttc    60
tgctgctgct gccgctgctg ccgccgctgt ccccgagcct tgggatccgc gacgtgggcg   120
gccggcgccc caagtgtggt ccgtgccggc cagagggctg cccggcgcct gcgccctgcc   180
cggcgcccgg gatctcggcg ctcgacgagt gcggctgctg cgcccgctgc ctgggagccg   240
agggcgcgag ctgcggggc cgcgccggcg ggcgctgtgg ccccggcctg gtatgcgcga   300
gccaggccgc tggggcagcg cccgagggca ccgggctctg cgtgtgcgcg cagcgcggca   360
ccgtctgcgg ctccgacggt cgctcgtacc ccagcgtctg cgcgctgcgc ctgcgcgctc   420
ggcacacgcc ccgcgcgcac cccggtcacc tgcacaaggc gcgcgacggc ccttgcgagt   480
tcgctcctgt ggtcgtcgtt cctccccgaa gtgttcacaa cgtcaccggg gcgcaggtgg   540
gcctgtcctg tgaagtgagg gctgtgccta ccccagtcat cacgtggaga aaggtcacga   600
agtccctga gggcacccaa gcactggagg agctgcctgg ggaccatgtc aatatagctg   660
tccaagtgcg aggggggccct tctgaccatg aggccacggc ctggattttg atcaaccccc   720
tgcgaaagga ggatgagggt gtgtaccagt gccatgcagc caacatggtg ggagaggctg   780
agtcccacag cacagtgacg gttctagatc tgagtaaata caggagcttc cacttcccag   840
ctcccgatga ccgcatgtga tggagaaatg gtcttagaaa cattgatcat gggatgatgg   900
aaaagtcaaa taacggatct ttgtgcttca tgaagagttg gaaaacctgt gtgtgtagat   960
gaccccttt gtgtgttttt aaaaattaga tgcaaactag atctgtatgc agatgtagtt  1020
tttagcaggg caaacagtga gaaacggatt tgcatgtggc tttttttatac ttttgaaatg  1080
aattgttcca tga                                                    1093

SEQ ID NO: 2           moltype = AA  length = 278
FEATURE                Location/Qualifiers
source                 1..278
                       mol_type = protein
                       organism = Homo sapiens
SEQUENCE: 2
MPRLSLLLPL LLLLLLPLLP PLSPSLGIRD VGGRRPKCGP CRPEGCPAPA PCPAPGISAL    60
DECGCCARCL GAEGASCGGR AGGRCGPGLV CASQAAGAAP EGTGLCVCAQ RGTVCGSDGR   120
SYPSVCALRL RARHTPRAHP GHLHKARDGP CEFAPVVVVP PRSVHNVTGA QVGLSCEVRA   180
VPTPVITWRK VTKSPEGTQA LEELPGDHVN IAVQVRGGPS DHEATAWILI NPLRKEDEGV   240
YQCHAANMVG EAESHSTVTV LDLSKYRSFH FPAPDDRM                          278

SEQ ID NO: 3           moltype = DNA  length = 725
FEATURE                Location/Qualifiers
source                 1..725
                       mol_type = genomic DNA
                       organism = Homo sapiens
SEQUENCE: 3
cttcagaagc aatgggaaaa atcagcagtc ttccaaccca attatttaag tgctgctttt    60
gtgatttctt gaaggtgaag atgcacacca tgtcctcctc gcatctcttc tacctggcgc   120
tgtgcctgct caccttcacc agctctgcca cggctggacc ggagacgctc tgcggggctg   180
agctggtgga tgctcttcag ttcgtgtgtg gagacagggg cttttatttc aacaagccaa   240
cagggtatgg ctccagcagt cggagggcgc ctcagacagg tatcgtggat gagtgctgct   300
tccggagctg tgatctaagg aggctggaga tgtattgcgc accctcaag cctgccaagt   360
cagctcgctc tgtccgtgcc cagcgccaca ccgacatgcc caagacccag aaggaagtac   420
attttgaagaa cgcaagtaga gggagtgcag gaaacaagaa ctacaggatg taggaagacc   480
ctcctgagga gtgaagagtg acatgccacc gcaggatcct ttgctctgca cgagttacct   540
gttaaacttt ggaacaccta ccaaaaaata agtttgataa catttaaaag atgggcgttt   600
cccccaatga aatacacaag taaacattcc aacattgtct ttaggagtga tttgcaccttt   660
gcaaaaatgg tcctggagtt ggtagattgc tgttgatctt ttatcaataa tgttctatag   720
aaaag                                                             725

SEQ ID NO: 4           moltype = AA  length = 306
FEATURE                Location/Qualifiers
source                 1..306
                       mol_type = protein
                       organism = Homo sapiens
SEQUENCE: 4
MGKISSLPTQ LFKCCFCDFL KVKMHTMSSS HLFYLALCLL TFTSSATAGP ETLCGAELVD    60
ALQFVCGDRG FYFNKPTGYG SSSRRAPQTG IVDECCFRSC DLRRLEMYCA PLKPAKSARS   120
VRAQRHTDMP KTQKEVHLKN ASRGSAGNKN YRMMGKISSL PTQLFKCCFC DFLKVKMHTM   180
SSSHLFYLAL CLLTFTSSAT AGPETLCGAE LVDALQFVCG DRGFYFNKPT GYGSSSRRAP   240
QTGIVDECCF RSCDLRRLEM YCAPLKPAKS ARSVRAQRHT DMPKTQKEVH LKNASRGSAG   300
NKNYRM                                                             306
```

What is claimed is:

1. A method of reducing severity of glaucoma in a subject in need thereof, the method comprising intravitreally administering to the subject a composition comprising an insulin-like growth factor binding protein-like 1 (IGFBPL-1) protein.

2. The method of claim 1, wherein the IGFBPL-1 protein comprises the amino acid sequence of SEQ ID NO: 2.

3. The method of claim 1, wherein the composition promotes outgrowth of a neuron.

4. The method of claim 3, wherein the neuron is an optic nerve neuron, a retinal ganglion cell, or a retinal neuron.

5. The method of claim 1, wherein the glaucoma is angle-closure glaucoma, open-angle glaucoma, secondary glaucoma or congenital glaucoma.

6. The method of claim 1, wherein reducing severity comprises improving the subject's vision.

7. A method of reducing severity of a neuronal injury in a subject in need thereof, the method comprising intravitreally administering to the subject a composition comprising an IGFBPL-1 protein, wherein the subject has glaucoma.

8. The method of claim 7, wherein the IGFBPL-1 protein comprises the amino acid sequence of SEQ ID NO: 2.

9. The method of claim 7, wherein the composition promotes outgrowth of a neuron.

10. The method of claim 9, wherein the neuron is an optic nerve neuron, a retinal ganglion cell, or a retinal neuron.

11. The method of claim 7, wherein the glaucoma is angle-closure glaucoma, open-angle glaucoma, secondary glaucoma or congenital glaucoma.

12. The method of claim 7, wherein reducing severity comprises improving the subject's vision.

* * * * *